United States Patent

Cummins et al.

[11] Patent Number: 5,811,295
[45] Date of Patent: Sep. 22, 1998

[54] DIAGNOSTIC COMPOSITIONS, ELEMENTS, METHODS AND TEST KITS FOR AMPLIFICATION AND DETECTION OF TWO OR MORE DNA'S USING PRIMERS HAVING MATCHED MELTING TEMPERATURES

[75] Inventors: Thomas J. Cummins, Rochester; Susan Melissa Atwood, Rush; Lynn Bergmeyer, Rochester; John Bruce Findlay, Rochester; John W. H. Sutherland, Rochester; JoAnne H. Kerschner, Rochester, all of N.Y.

[73] Assignee: Johnson & Johnson Clinical Diagnostics, Inc., Rochester, N.Y.

[21] Appl. No.: 495,742

[22] Filed: Jun. 8, 1995

Related U.S. Application Data

[62] Division of Ser. No. 62,023, May 14, 1993.

[51] Int. Cl.⁶ .................. A01N 1/02; C12Q 1/68
[52] U.S. Cl. ............................ 435/283.1; 435/6
[58] Field of Search ............ 435/283.1, 6, 91.1, 435/91.2; 436/89

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,889,818 | 12/1989 | Gelfand et al. | 435/194 |
| 4,965,188 | 10/1990 | Mullis et al. | 435/6 |
| 5,008,182 | 4/1991 | Sninsky et al. | 435/5 |
| 5,079,351 | 1/1992 | Sninsky et al. | 536/27 |
| 5,147,777 | 9/1992 | Sutton et al. | 435/5 |
| 5,173,260 | 12/1992 | Zander et al. | 422/57 |
| 5,176,995 | 1/1993 | Sninsky et al. | 435/6 |
| 5,196,305 | 3/1993 | Findlay et al. | 435/6 |
| 5,229,297 | 7/1993 | Schnipelsky et al. | 436/94 |

FOREIGN PATENT DOCUMENTS

| | | |
|---|---|---|
| 435150A3 | 12/1990 | European Pat. Off. . |
| 469610A1 | 8/1991 | European Pat. Off. .......... C12Q 1/68 |
| 481215A1 | 9/1991 | European Pat. Off. . |
| 0511712A1 | 4/1992 | European Pat. Off. .......... C12Q 1/68 |
| 516540A1 | 5/1992 | European Pat. Off. . |
| 90/08840 | 8/1990 | WIPO . |
| 92/16659 | 10/1992 | WIPO . |

OTHER PUBLICATIONS

Urdea et al, Nucleic Acid Res 16:4937–4956 (1988).
Nedjar e al., J. Virol. Meth., 35, pp. 297–304 (1991).
Jackson et al., N. England J. Med., 322 (4), pp. 217–222 (1990).
PCR Protocols: A Guide to Methods & Applications Chp. 40, Kellog & Kwok, Academic Press 1990.
Hewlett et al., Oncogene, 4, pp. 1149–1151 (1989).
Coutlee et al., Molecular & Cellular Probes, 3, pp. 241–259 (1991).
Chow, J. Clin. Microbiol., 30(9), pp. 2307–2310 (1992).
Frank et al., Modern Patholoty, 5(4), pp. 449–454 (1992).
Sokol et al., J. Clin. Microbiol., 30(4), pp. 839–844 (1992) (1991).
Brytting et al., J. Viro. Methods, 32, pp. 127–138 (1991).
Demmler et al., J. Infect. Diseases, 158(6), pp. 1177–1184 (1988).
Porter–Jordan et al., J. Med. Virol., 30, pp. 85–91 (1990).
Fenner et al., J. Clin. Microbiol., 29(11), pp. 2621–2622 (1991).
Hsia et al., J. Clin. Microbiol., 27(8), pp. 1802–1809 (1989).
Gibbs et al., Genomics, 7, pp. 235–244 (1990).
Mullis et al. Cold Spr. Hrb. Syn. L1; pp. 263–273 (1986).
Matthews et al., Anal. Biochem., 169, pp. 1–25 (1988).
Spaete et al., Virology, 167, pp. 207–225 (1988).
Vandenvelde et al., J. Virol. Metho., 30, pp. 215–228 (1990).

*Primary Examiner*—Eggerton A. Campbell

[57] ABSTRACT

An aqueous composition containing primers for opposing strands of two or more target nucleic acids can be used in polymerase chain reaction to provide simultaneously rapid and efficient amplification and detection of those nucleic acids. The primers for each target DNA differ in length by no more than 5 nucleotides and have a $T_m$ within the range of from about 65° to about 74° C., while the $T_m$'s are within about 5° C. of each other. Such compositions are useful in diagnostic test kits and methods for amplification and detection of multiple nucleic acids, or in "multiplexing", using multiple capture probes. All of the capture probes have $T_m$'s which are greater than 50° C. and are within 15° C. of each other.

1 Claim, 7 Drawing Sheets

DIAGNOSTIC COMPOSITIONS, ELEMENTS, METHODS AND TEST KITS FOR AMPLIFICATION AND DETECTION OF TWO OR MORE DNA'S USING PRIMERS HAVING MATCHED MELTING TEMPERATURES

This is a division of application Ser. No. 08/062,023, filed May 14, 1993, which is hereby incorporated by reference.

FIELD OF THE INVENTION

This invention relates to diagnostic compositions, elements, methods and test kits for the amplification and detection of a multiplicity of nucleic acids associated with one or more infectious agents. In particular, it relates to improved methods of polymerase chain reaction (PCR) using test kits and buffered compositions containing "matched" primers for a bacterial or viral DNA.

BACKGROUND OF THE INVENTION

Technology to detect minute quantities of nucleic acids associated with various infectious agents (including viruses, bacteria, fungus and protozoa) has advanced rapidly over the last ten years including the development of highly sophisticated hybridization assays using probes in amplification techniques such as PCR. Researchers have readily recognized the value of such technology to detect diseases and genetic features in human or animal test specimens. The use of probes and primers in such technology is based upon the concept of complementarity, that is the bonding of two strands of a nucleic acid by hydrogen bonds between complementary nucleotides (also known as nucleotide pairs).

PCR is a significant advance in the art to allow detection of very small concentrations of a targeted nucleic acid. The details of PCR are described, for example, in U.S. Pat. No. 4,683,195 (Mullis et al), U.S. Pat. No. 4,683,202 (Mullis), and U.S. Pat. No. 4,965,188 (Mullis et al) and by Mullis et al, *Methods of Enzymology*, 155, pp. 335–350 (1987), although there is a rapidly expanding volume of literature in this field. Without going into extensive detail, PCR involves hybridizing primers to the strands of a targeted nucleic acid (considered "templates") in the presence of a polymerization agent (such as a DNA polymerase) and deoxyribonucleoside triphosphates under the appropriate conditions. The result is the formation of primer extension products along the templates, the products having added thereto nucleotides which are complementary to the templates.

Once the primer extension products are denatured, one copy of the templates has been prepared, and the cycle of priming, extending and denaturation can be carried out as many times as desired to provide an exponential increase in the amount of nucleic acid which has the same sequence as the target nucleic acid. In effect, the target nucleic acid is duplicated (or "amplified") many times so that it is more easily detected. Despite the broad and rapid use of PCR in a variety of biological and diagnostic fields, there are still practical limitations which must be overcome to achieve the optimum success of the technology.

It is well known that PCR is susceptible to a "carry-over" problem whereby amplified nucleic acids from one reaction may be inadvertently carried over into subsequent reactions using "fresh" PCR reaction mixtures, and thereby causing "false" positives when testing later specimens.

One approach to this problem is to completely contain the reagents for each PCR procedure so no reagents or by-products can be carried over into later reactions. Specially designed test packs or test devices have been designed to contain PCR procedures for this reason. Such test packs are described, for example, in recently allowed U.S. Ser. No. 07/962,159 [filed Oct. 15, 1992 by Schnipelsky et al as a continuation of U.S. Ser. No. 07/673,053 (filed Mar. 21, 1991, now abandoned) which in turn is a CIP of U.S. Ser. No. 07/339,923 (filed Apr. 17, 1989, now abandoned) which in turn is a CIP of U.S. Ser. No. 07/306,735 (filed Feb. 3, 1989, now abandoned)]. These test devices are preferably, but not necessarily, used in PCR in combination with automatic PCR processing equipment such as that described in U.S. Pat. No. 5,089,660 (Devaney Jr.) and in U.S. Pat. No. 5,089,233 (Devaney Jr. et al). This equipment is characterized by its capability to simultaneously process several test specimens in separate test devices.

More preferably, it would be desirable to detect a multiplicity of target nucleic acids (or a multiplicity of nucleic acid sequences in the same nucleic acid) in a single test device. This is referred to herein as "multiplexing".

In one embodiment of PCR, a specific set of primers and a capture probe (a total of three oligonucleotides) are needed for each target nucleic acid which is to be amplified and detected. Thus, the three oligonucleotides are complementary and specific to that target nucleic acid. For example, in multiplexing, if three target nucleic acids are to be amplified and detected, typically three sets of primers and probes are needed, one set specific for each target nucleic acid. Normally, detection of the multiple nucleic acids requires a multiplicity of test devices, and perhaps different sets of PCR conditions (that is, temperature and time conditions) to obtain efficient amplification of each target nucleic acid.

It would be desirable, however, to amplify and detect a plurality of target nucleic acids simultaneously in the same test device, using "universal" processing equipment and conditions. This cannot be done by merely selecting any set of primers and probes specific for each target nucleic acid from conventional sources. Where processing equipment is used to process several test devices simultaneously, or a single test device is designed for multiplexing, the equipment must be somehow adapted to provide optimum heating and cooling times and temperatures for each set of primers and probes, since they will all likely have individual optimum amplification conditions (for example, denaturation temperatures). To adapt the equipment to randomly selected primers and probes in multiplexing would be a very expensive and cumbersome solution to the problem. Yet there is a great need for efficient, relatively inexpensive and rapid multiplexing to detect multiple nucleic acids, or two or more nucleic acid sequences of the same nucleic acid.

SUMMARY OF THE INVENTION

The problems noted above are overcome by using, in PCR, an aqueous composition buffered to a pH of from about 7 to about 9, which comprises:

a) first and second primers which are specific to and hybridizable with, respectively, first and second nucleic acid sequences which are in opposing strands of a first target DNA and which are separated from each other along the opposing strands by from 90 to 400 nucleotides, and b) third and fourth primers which are specific to and hybridizable with, respectively, third and fourth nucleic acid sequences which are in opposing strands of a second target DNA which is the same as or different from the first target DNA, the third and fourth nucleic acid sequences being different from the first and second nucleic acid sequences and being separated from each other along the opposing strands by from 90 to 400 nucleotides, each of the first, second, third and fourth primers having a $T_m$ within the range of from about 65° to about 74° C., all of the primer $T_m$'s being within about 5° C. of each other, the first and second primers having nucleotide lengths which differ from each other by no more than 5 nucleotides, and the third and fourth primers having nucleotide lengths which differ from each other by no more than 5 nucleotides.

This invention also provides a diagnostic test kit for the amplification of a first target DNA comprising, in separate packaging:

a) an aqueous composition buffered to a pH of from about 7 to about 9, which comprises:

first and second primers which are specific to and hybridizable with, respectively, first and second nucleic acid sequences which are in opposing strands of a first target DNA and which are separated from each other along the opposing strands by from 90 to 400 nucleotides, and third and fourth primers which are specific to and hybridizable with, respectively, third and fourth nucleic acid sequences which are in opposing strands of a second target DNA which is the same as or different from the first DNA, the third and fourth nucleic acid sequences being different from the first and second nucleic acid sequences and being separated from each other along the opposing strands of the second target DNA by from 90 to 400 nucleotides, each of the first, second, third and fourth primers having a $T_m$ within the range of from about 65° to about 74° C., all of the primer $T_m$'s being within about 5° C. of each other, the first and second primers having nucleotide lengths which differ from each other by no more than 5 nucleotides, and the third and fourth primers having nucleotide lengths which differ from each other by no more than 5 nucleotides, and b) at least one additional PCR reagent.

A method of this invention for the simultaneous amplification and detection of a first target DNA and a second target DNA comprises:

A) simultaneously subjecting the denatured opposing strands of a first target DNA and the denatured opposing strands of a second target DNA to polymerase chain reaction in the presence of:

i) an aqueous composition buffered to a pH of from about 7 to about 9, and comprising:

first and second primers which are specific to and hybridizable with, respectively, first and second nucleic acid sequences which are in opposing strands of the first target DNA and which are separated from each other along the opposing strand by from 90 to 400 nucleotides, third and fourth primers which are specific to and hybridizable with, respectively, third and fourth nucleic acid sequences which are in opposing strands of the second target DNA which is the same as or different from the first target DNA, the third and fourth nucleic acids sequences being separated from each other along the opposing strands of the second target DNA by from 90 to 400 nucleotides, each of the first, second, third and fourth primers having a $T_m$ within the range of from about 65° to about 74° C., all of the primer $T_m$'s being within about 5° C. of each other, the first and second primers having nucleotide lengths which differ from each other by no more than 5 nucleotides, and the third and fourth primers having nucleotide lengths which differ from each other by no more than 5 nucleotides, and ii) the additional PCR reagents: a thermostable DNA polymerase, a DNA polymerase cofactor and at least one dNTP, any or all of the additional PCR reagents being in the same or a different composition as defined in i), to simultaneously amplify the opposing first target DNA strands and the opposing second target DNA strands, B) simultaneously detecting at least one of the amplified first target DNA strands and at least one of the amplified second target DNA strands as a simultaneous determination of the presence of the first and second target DNA's.

The present invention provides an effective and efficient means for multiplexing, or amplifying and detecting a multiplicity of target nucleic acid sequences using the same test device, if desired, and the same processing equipment (processing one or more test devices simultaneously). It is particularly useful for the detection of one or more nucleic acid sequences of a first DNA associated with an infectious agent and one or more nucleic acid sequences of a second target DNA associated with the same or another infectious agent. Any number of nucleic acid sequences of the same or different DNA molecules can be amplified and determined simultaneously using the appropriate primer sets in combination.

These advantages are achieved by using a set of "matched" primers in PCR for each target nucleic acid. By "matched" primers is meant primers in each set having melting temperatures ($T_m$'s) which are essentially the same, that is they differ by no more than about 5° C. Moreover, the $T_m$'s of the two primers of each set are within the range of from about 65° to about 74° C., and the two primers in each primer set have nucleotide lengths which differ from each other by no more than 5 nucleotides. Further, all of the primers of all primer sets used in an amplification method are also "matched", that is, they all have $T_m$'s which differ by no more than about 5° C. and all are within the range of from about 65° to about 74° C.

DETAILED DESCRIPTION OF THE INVENTION

Figure 1:
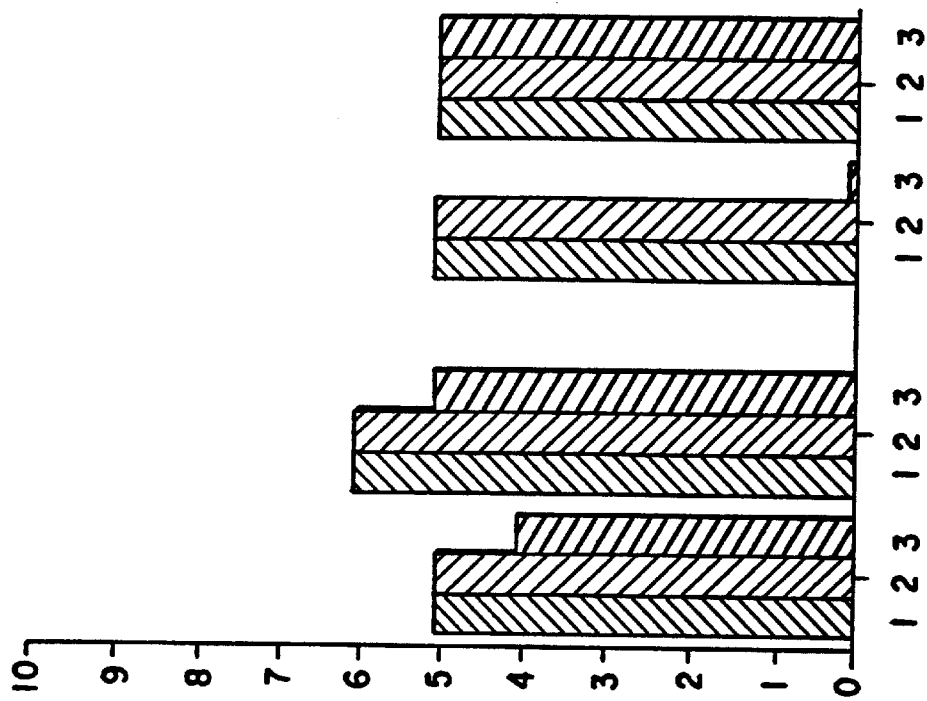
FIGS. 1–6 are sets of bar graphs showing dye signals for replicate PCR assays of various concentrations of both of hCMV DNA and HIV-I DNA, as described in Example 2 below.
Figure 2:
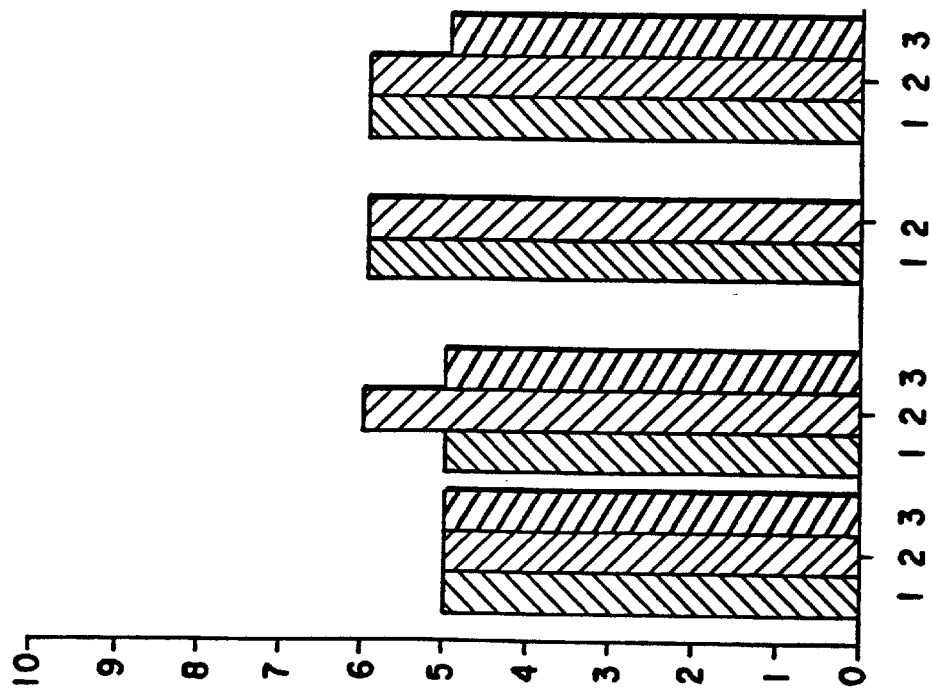
Figure 4:
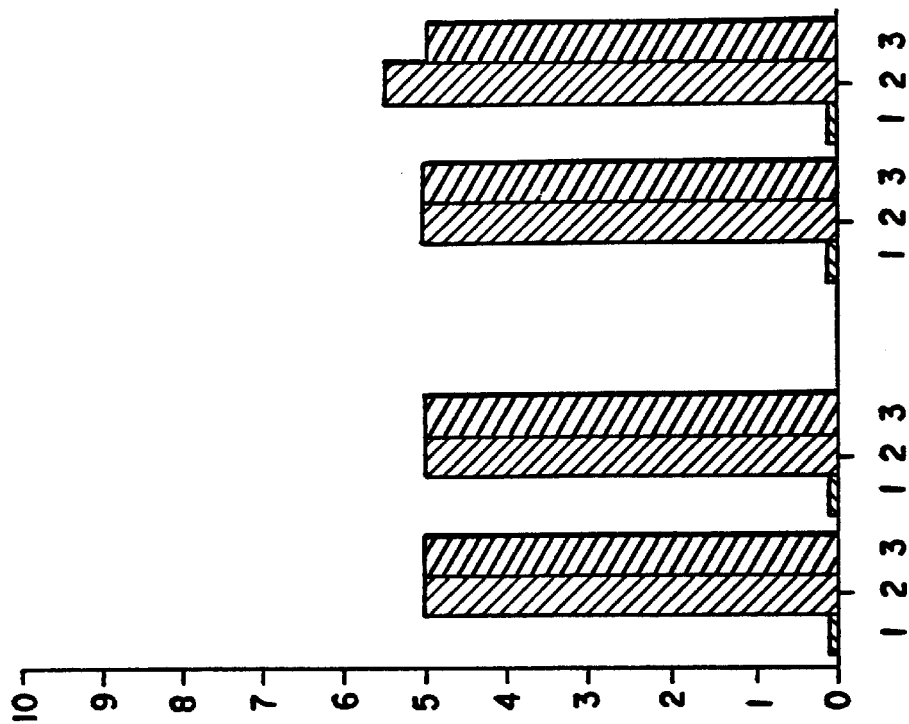
Figure 3:
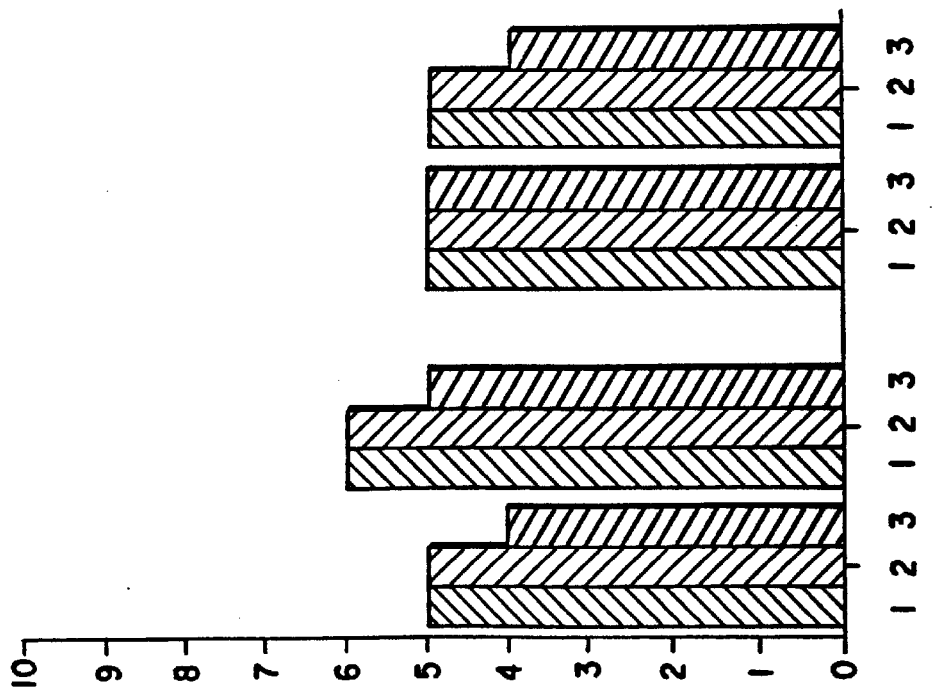
Figure 5:
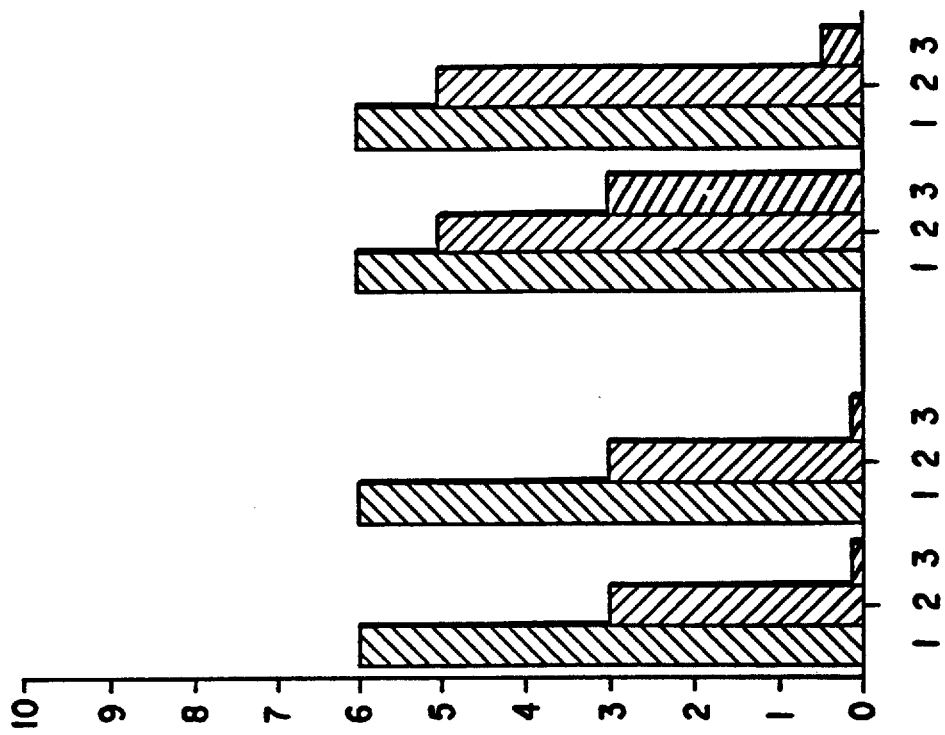
Figure 6:
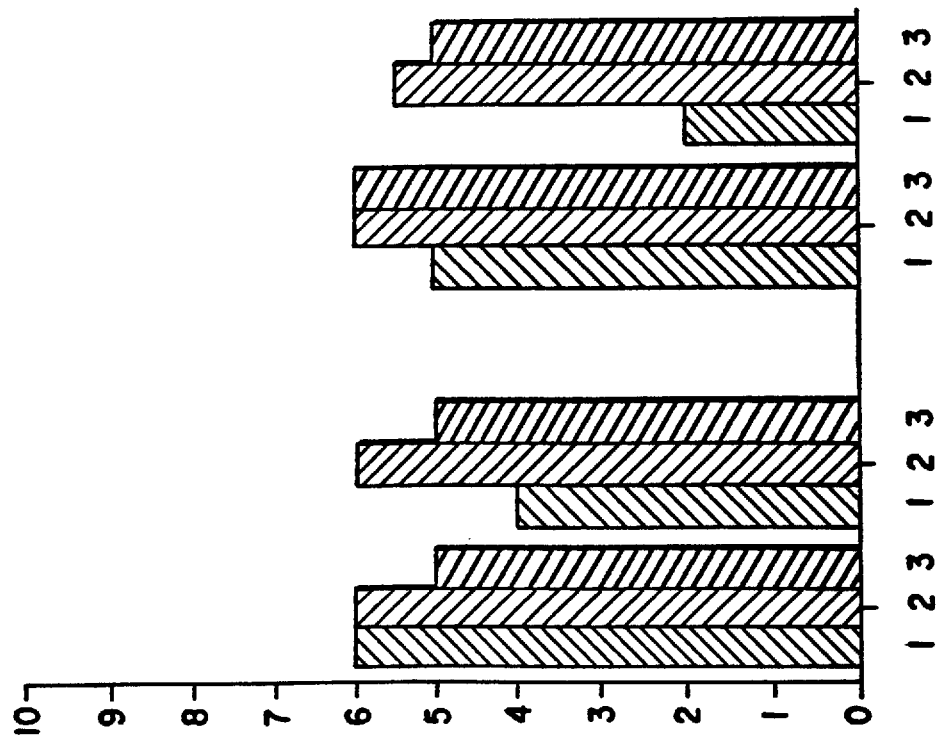

The general principles and conditions for amplification and detection of nucleic acids using polymerase chain reaction are quite well known, the details of which are provided in numerous references including U.S. Pat. No. 4,683,195, U.S. Pat. No. 4,683,202, U.S. Pat. No. 4,965,188, the disclosures of which are incorporated herein by reference. Thus, many details of PCR are not included herein. In view of the teaching in the art and the specific teaching provided herein, a worker skilled in the art would have no difficulty in practicing the present invention by making the adjustments taught herein to accomplish simultaneous amplification and detection of two or more target DNA's.

The present invention is directed to the amplification and detection of two or more specific nucleic acid sequences from DNA molecules associated with infectious agents in a test specimen. Such specimens can include bacterial or viral material, hair, body fluids or cellular materials containing DNA which can be detected.

Nucleic acids to be amplified and detected can be obtained from various sources including plasmids and naturally occurring DNA or RNA from any source (such as bacteria, yeast, viruses, plants, higher animals and humans). It may be extracted from various tissues including peripheral blood mononuclear cells and other blood components, tissue material or other sources known in the art using known procedures.

The method described herein is particularly useful for the detection of infectious agents, such as bacteria, viruses, fungi and protozoa, by detection of nucleic acids associated therewith.

Bacteria which can be detected include, but are not limited to, bacteria found in human blood, Salmonella species, Streptococcus species, Chlamydia species, Gonococcal species, *Mycobacterium tuberculosis, Mycobacterium fortuitum, Mycobacterium avium complex, Legionella pneumophila, Clostridium difficile, Borrelia burgdorferei, Pneumocystis carinii, Mycoplasma Haemophilus influenzae,* Shigella species and Listeria species. Viruses which are detectable, besides cytomegalovirus, include, but are not limited to, herpes, Epstein Barr virus, influenza viruses, human papilloma virus, hepatitis and retroviruses such as HTLV-I, HTLV-II, HIV-I and HIV-II. Protozoan parasites, yeasts and molds are also detectable. Other detectable species would be readily apparent to one skilled in the art.

The invention is useful for the simultaneous amplification and detection of one or more nucleic acid sequences of a retroviral DNA (such as HTLV-I, HTLV-II, HIV-I or HIV-II DNA), human cytomegaloviral (hCMV) DNA, human papilloma viral DNA, *Mycobacterium tuberculosis* DNA, *Mycobacterium avium* DNA, hepatitis viral DNA and *Pneumocystis carinii* DNA.

A "target" DNA as used in this application also includes nucleic acids which are added to a test specimen to provide positive controls in the assays.

A "PCR reagent" refers to any of the reagents considered essential to PCR, namely primers for the target nucleic acid, a thermostable DNA polymerase, a DNA polymerase cofactor, and one or more deoxyribonucleoside-5'-triphosphates. Other optional reagents and materials used in PCR are described below.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of nucleotides (such as the four standard deoxyribonucleoside-5'-triphosphates), a thermostable DNA polymerase and a DNA polymerase cofactor, and suitable temperature and pH.

The primer is preferably single stranded for maximum efficiency in amplification, but can contain a double stranded region if desired. It must be long enough to prime the synthesis of extension products in the presence of the DNA polymerase. The exact size of each primer will vary depending upon the use contemplated, the complexity of the targeted sequence, reaction temperature and the source of the primer. Generally, the primers used in this invention will have from 12 to 60 nucleotides, and preferably, they have from 20 to 40 nucleotides. More preferably, each primer in a set has from 25 to 35 nucleotides. The lengths of the primers in each primer set differ from each other by no more than 5 nucleotides, and preferably by no more than 2 nucleotides. Most preferably, the primers within a set have the same length.

One set of primers used in the practice of the invention includes first and second primers which are specific to, respectively, first and second nucleic acid sequences in opposing strands of a first target DNA. The first and second sequences are spaced along the opposing strands from each other by from 90 to 400 nucleotides, and preferably from 100 to 300 nucleotides apart on opposing strands. Thus, the two primers hybridize to nucleic acid sequences which are relatively close to each other along the opposing strands.

A second set of primers (including third and fourth primers) is used to amplify and detect third and fourth sequences of opposing strands of the same target DNA or of another target DNA from a different source. Additional sets of primers can be used to amplify and detect additional target DNA's.

For every set of primers used in this invention, each primer in the set has a $T_m$ within the range of from about 65° to about 74° C., and preferably within the range of from about 67° to about 74° C. In addition, the primer $T_m$'s are within about 5° C. of each other, and preferably they differ by no more than 2° C. Further still, the $T_m$'s of the primers in each additional set differ from the $T_m$'s of all other primers in the other sets of primers used in the method by no more than about 5° C., and preferably by no more than about 2° C. The additional primers also hybridize to nucleic acid sequences in the opposing strands of the particular target nucleic acid, which sequences are spaced apart along the strands by from 90 to 400 nucleotides (more preferably, from 100 to 300 nucleotides apart).

These characteristics and relationships among all of the primers allow for effective and efficient multiplexing using the same PCR processing equipment and conditions.

$T_m$ (melting temperature) is defined herein as the temperature at which one-half of a double stranded DNA molecule is denatured. The determination of $T_m$ can be accomplished using several standard procedures, based on ultraviolet hypochromism, for example, by monitoring the spectrum at 260 nm as described in *Biochemistry—The Molecular Basis of Cell Structure and Function,* 2nd Edition, Lehninger, Worth Publishers, Inc., 1970, pp. 876–7. The various methods of determining $T_m$ values may produce slightly differing values for the same DNA molecule, but those values should not vary from each other by more than about 2° or 3° C.

Preferably, the $T_m$ values described herein for the primers and probes are calculated using the formula (I):

$$T_m(°C.)=67.5+0.34(\%G+C)-395/N \qquad (I)$$

wherein "G" and "C" represent the number of guanine and cytosine nucleotides, respectively, and "N" represents the total number of nucleotides in the oligonucleotide (that is, primer or probe). $T_m$ values obtained by this calculation correlate very well with the values determined empirically at room temperature using conventional UV hypochromism and a conventional Hewlett-Packard diode array spectrophotometer (scanning rate of about +1° C./min.) for a solution of oligonucleotide (primer or probe) in 10 mmolar tris(hydroxymethyl)aminomethane buffer (pH 8.5) having an ionic strength of at least about 60 mmolar provided by one or more inorganic or organic salts, such as magnesium chloride, magnesium sulfate, potassium chloride, sodium chloride, and others readily apparent to one skilled in the art. The amount of oligonucleotide and its complement in the solution used to determine the noted formula was sufficient to provide an optical density of from about 0.5 to about 1.0 OD units.

The primers used in the present invention are selected to be "substantially complementary" to the specific nucleic acid sequences to be primed and amplified. This means that they must be sufficiently complementary to hybridize with the respective nucleic acid sequences to form the desired hybridized products and then be extendable by a DNA polymerase. In the preferred and most practical situation, the primers have exact complementarity to the nucleic acid sequences of interest.

Primers useful for the amplification and detection of HIV-I DNA include, but are not limited to, those having the sequences in the seven primer sets shown below with the $T_m$ in parenthesis:

Primer set 1:
SEQ ID:NO:1 5'-AGTGGGGGGA CATCAAGCAG CCATGCAA-3' (72.8° C.)
SEQ ID:NO:2 5'-TTCCTGCTAT GTCACTTCCC CTTGGTTC-3' (70.4° C.),
Primer set 2:
SEQ ID:NO:3 5'-TAGCACCCAC CAGGGCAAAG AGAAGAGT-3' (71.6° C.)
SEQ ID:NO:4 5'-AGATGCTGTT GCGCCTCAAT AGCCCTCA-3' (72.1° C.),
Primer set 3:
SEQ ID:NO:1 5'-AGTGGGGGGA CATCAAGCAG CCATGCAA-3' (72.8° C.)
SEQ ID:NO:5 5'-CTTGGTTCTC TCATCTGGCC TGGTGC-3' (71.6° C.),
Primer set 4:
SEQ ID:NO:1 5'-AGTGGGGGGA CATCAAGCAG CCATGCAA-3' (72.8° C.)
SEQ ID:NO:13 5'-CCTGCTATGT CACTTCCCCT TGGTTCTCTC-3' (72.5° C.),
Primer set 5:
SEQ ID:NO:20 5'-CGTCGTCGTA TAATCCACCT ATCCCAGTAG GAGAAAT-3' (71.3° C.),
SEQ ID:NO:21 5'-CGTCGTCGTT TTGGTCCTTG TCTTATGTCC AGAATGC-3' (73.4° C.),
Primer set 6:
SEQ ID:NO:22 5'-ATAATCCACC TATCCCAGTA GGAGAAAT-3' (66.8° C.),
SEQ ID:NO:23 5'-TTTGGTCCTT GTCTTATGTC CAGAATGC-3' (68.0° C.), and
Primer set 7:
SEQ ID:NO:24 5'-GATGGATGAC AAATAATCCA CCTATCCCAG TAGGAGAAAT-3' (71.2° C.),
SEQ ID:NO:25 5'-CTAAAGGGTT CCTTTGGTCC TTGTCTTATG TCCAGAATGC-3' (72.9° C.).

The primers of sets 1 and 3–7 are complementary to nucleic acid sequences in the "gag" region of HIV-I DNA, and the primers in set 2 are complementary to nucleic acid sequences in the "env" region of HIV-I DNA. Each primer in each set is not limited to use in that set, but can be used with any primer specific to HIV-I DNA that meets the requirements for primers described herein.

Two primer sets useful for the amplification of nucleic acid sequences in opposing strands of HIV-II DNA have the following sequences (and $T_m$'s):

Primer set 8:
SEQ ID:NO:14 5'-AAGTAGACCA ACAGCACCAC CTAGCGG-3' (71.8° C.)
SEQ ID:NO:15 5'-GCAGCCTTCT GAGAGTGCCT GAAATCCTG-3' (72.6° C.), and Primer set 9:
SEQ ID:NO:16 5'-GGGATAGTGC AGCAACAGCA ACAGCTGT-3 (71.6° C.)
SEQ ID:NO:17 5'-GTGGCAGACT TGTCTAAACG CACATCCCC-3' (72.6° C.).

Primers of particular usefulness in the amplification and detection of hCMV DNA include, but are not limited to, those having the sequences in the three primer sets shown below with the $T_m$ in parenthesis:
Primer set 10:
SEQ ID NO:46: 5'-GAGGCTATTG TAGCCTACAC TTTGG-3' (68.0° C.)
SEQ ID NO:47: 5'-CAGCACCATC CTCCTCTTCC TCTGG-3' (72.1° C.),
Primer set 11:
SEQ ID:NO:38 5'-CATTCCCACT GACTTTCTGA CGCACGT-3' (70.5° C.)
SEQ ID:NO:48 5'-TGAGGTCGTG GAACTTGATG GCGT-3' (69.4° C.),
and
Primer set 12:
SEQ ID NO:10: 5'-TGCACTGCCA GGTGCTTCGG CTCAT-3' (72.1° C.)
SEQ ID NO:11: 5'-CACCACGCAG CGGCCCTTGA TGTTT-3' (72.1° C.).

The primers of Set 10 are complementary to nucleic acid sequences in the "major immediate early" region of hCMV DNA, the primers in Set 11 are complementary to nucleic acid sequences in the "major capsid protein" region of hCMV DNA, and the primers in Set 12 are complementary to nucleic acid sequences in the "late antigen" region of hCMV DNA. The primers noted above are not limited in use to the particular set, but can be used with any primer for hCMV DNA which has the properties noted herein.

Matched primers useful for the amplification of human papilloma virus (hPV) DNA include, but are not limited to:
Primer set 13:
SEQ ID:NO:26 5'-GAGATGGGAA TCCATATGCT GTATGTGAT-3' (68° C.)
SEQ ID:NO:27 5'-GGACACAGTG GCTTTTGACA GTTAATACA-3' (68° C.),
Primer set 14:
SEQ ID:NO:28 5'-GATGGTCCAG CTGGACAAGC AGAAC-3' (70.7° C.)
SEQ ID:NO:29 5'-CCTAGTGTGC CCATTAACAG GTCTTC-3' (69.3° C.),
Primer set 15:
SEQ ID:NO:30 5'-GACACAGAAA ATGCTAGTGC TTATGCAGC-3' (69.1° C.)
SEQ ID:NO:31 5'-GGTGGACAAT CACCTGGATT TACTGCAAC-3' (70.3° C.),
Primer set 16:
SEQ ID:NO:32 5'-CCTGATCTGT GCACGGAACT GAACACT-3' (70.5° C.)
SEQ ID:NO:33 5'-CCCAGTGTTA GTTAGTTTTT CCAATGTGTC TG-3' (69° C.),
Primer set 17:
SEQ ID:NO:34 5'-TGCCTGCGGT GCCAGAAACC GTTGAAT-3' (71.8° C.)
SEQ ID:NO:35 5'-TGCTCGGTTG CAGCACGAAT GGCACT-3' (71.9° C.),
Primer set 18:
SEQ ID:NO:36 5'-GAGCCGAACC ACAACGTCAC ACAATGTT-3' (70.4° C.)
SEQ ID:NO:37 5'-GGACACACAA AGGACAGGGT GTTCAGAAA-3' (70.3° C.), and Primer set 19:
SEQ ID:NO:37 5'-GGACACACAA AGGACAGGGT GTTCAGAAA-3' (70.3° C.)
SEQ ID:NO:39 5'-GCGACTCAGA GGAAGAAAAC GATG-3' (68° C.).

Matched primers useful for the amplification of Mycobacterium tuberculosis (Mtb) DNA include, but are not limited to:
Primer set 20:
SEQ ID:NO:40 5'-GAGATCGAGC TGGAGGATCC GTACG-3' (72.1° C.)
SEQ ID:NO:41 5'-AGCTGCAGCC CAAAGGTGTT GGACT-3' (70.7° C.), and
Primer set 21:
SEQ ID:NO:42 5'-TCAGCCGCGT CCACGCCGCG A-3' (75° C.)
SEQ ID:NO:43 5'-CCTGCGAGCG TAGGCGTCGG-3' (73.3° C.).

SEQ ID:NO:42 is slightly outside the claimed range of matched primers, but PCR is still possible using it, although not as efficiently for "multiplexing".

A matched primer set useful for the amplification of Mycobacterium avium (Mav) DNA, is as follows:
Primer set 22:
SEQ ID:NO:44 5'-GAGATCGCCA CCTTCGGCAA-3' (68.2° C.)
SEQ ID:NO:45 5'-GAGCAGTTCG GTGGCGTTCA-3' (68.2° C.).

A matched primer set useful for the amplification of the thymidine kinase gene of Herpes simplex virus 1 (HSV-1) DNA is as follows:
Primer set 23:
SEQ ID:NO:63 5'-CCGGGAGATG GGGGAGGCTA ACTGA-3' (73.5° C.)
SEQ ID:NO:64 5'-GGGGTGGGGA AAAGGAAGAA ACGCG-3' (72.1° C.).

Primers useful for the amplification and detection of additional target nucleic acids would be readily determinable by a skilled worker in the art by consultation with the considerable literature in this field to determine appropriate nucleic acid sequences of target nucleic acids. Those sequences can then be used as patterns for preparing primers using known technology. The primers can be readily screened by determining if they have the requisite $T_m$ (using appropriate methods defined above) and other requirements as defined above.

Primers useful herein can be prepared using known techniques and equipment, including for example, an ABI DNA Synthesizer (available from Applied Biosystems) or a Biosearch 8600 Series or 8800 Series Synthesizer (available from Milligen-Biosearch, Inc.). Procedures for using this equipment are well known and described for example in U.S. Pat. No. 4,965,188, incorporated herein by reference. Naturally occurring primers isolated from biological sources may also be useful (such as restriction endonuclease digests).

As used herein, a "probe" is an oligonucleotide which is substantially complementary to a nucleic acid sequence of the target nucleic acid (for example, HIV-I DNA or any additional target nucleic acid) and which is used for detection or capture of the amplified target nucleic acid. The probes generally have from 10 to 40 nucleotides, and a $T_m$ greater than about 50° C. Moreover, the probes are hybridizable with a nucleic acid sequence of the particular target nucleic acid at a temperature in the range of from about 40° to about 55° C. (preferably in the range of from about 45° to about 53° C.). In the use of a multiplicity of probes for simultaneously capturing a multiplicity of amplified target nucleic acids in the practice of this invention, all of the capture probes have $T_m$'s which differ by no more than about 15° C. Preferably, the capture probe $T_m$'s used simultaneously differ by no more than about 5° C.

Representative capture probes for HIV-I DNA include, but are not limited to, the following oligonucleotides, with the $T_m$'s in parenthesis:
SEQ ID:NO:6 5'-GAGACCATCA ATGAGGAAGC TGCAGAAT-3' (69.2° C.), and
SEQ ID:NO:7 5'-GTGCAGCAGC AGAACAATTT GCTGAGGG-3' (71.6° C.).

The first listed probe is complementary to a nucleic acid sequence in the the "gag" region of HIV-I DNA, and the second listed probe is complementary to a nucleic acid sequence in the "env" region of HIV-I DNA.

Representative capture probes useful in the detection of an amplified nucleic acid sequence of HIV-II DNA include, but are not limited to, the following (with $T_m$):
SEQ ID:NO:18 5'-GAGGAAAAGA AGTTCGGGGC AGAAGT-3' (69.3° C.), and
SEQ ID:NO:19 5'-CAACAAGAAA TGTTGCGACT GACCGTCT-3' (69.2° C.).

Representative useful capture probes for hCMV DNA include, but are not limited to, the following oligonucleotides, with the $T_m$ in parenthesis:
SEQ ID:NO:8 5'-GGTGTCACCC CCAGAGTCCC CTGTACCCGC-3' (78.1° C.),
SEQ ID:NO:49 5'-GACACAGTGT CCTCCCGCTC CTCCTGAGCA-3' (75.9° C.),
SEQ ID:NO:50 5'-GTGGAAGGCG GCTCGCTGGA AGCCGGTCGT-3' (78.1° C.),
SEQ ID:NO:12 5'-GAACCGAGGG CCGGCTCACC TCTATGTTGG-3' (75.9° C.), and
SEQ ID:NO:62 5'-GGTCATCGCC GTAGTAGATG CGTAAGGCCT-3' (73.6° C.).

The first two listed probes are complementary to nucleic acid sequences in the "major immediate early" region of hCMV DNA, the next two listed probes are complementary to nucleic acid sequences in the "late antigen" region of hCMV DNA, and the last probe is complementary to a nucleic acid sequence in the "major capsid protein" region of hCMV DNA.

Representative probes useful for the detection of human papilloma viral (hPV) DNA include, but are not limited to:
SEQ ID:NO:51 5'-GGAACAACAT TAGAACAGCA ATA-CAACAAA CCG-3' (68.9° C.),
SEQ ID:NO:52 5'-AATATTGTAA CCTTTTGTTG CAAGTGTGAC TC-3' (66.8° C.),
SEQ ID:NO:53 5'-CCTATAGGTG GTTTGCAACC AATTAAACAC-3' (67.9° C.),
SEQ ID:NO:54 5'-GAGGTATTTG AATTTGCATT TAAA-GATTTA TTTGT-3' (63.8° C.),
SEQ ID:NO:55 5'-GCAAGACAGT ATTGGAACTT ACAGAGG-3' (68° C.), and
SEQ ID:NO:56 5'-GTGTTGTAAG TGTGAAGCCA GATTTGA-3' (66.7° C.).

Capture probes useful for the detection of Mycobacterium tuberculosis (Mtb) DNA include, but are not limited to:
SEQ ID:NO:57 5'-GAGCAGATTG CGGCCACCGC AGCGATTTCG-3' (75.9° C.), and
SEQ ID:NO:58 5'-CTCGTCCAGC GCCGCTTCGG-3' (73.3° C.).

Useful capture probes for the detection of Mycobacterium avium (Mav) DNA include, but are not limited to:
SEQ ID:NO:59 5'-TGGATCTCGT TGTTCGGGTC-3' (66.5° C.), and

SEQ ID:NO:60 5'-GACCAGATCG CTGCCACCGC GGCCATCTCC-3' (78.1° C.).

A useful capture probe for the detection of Mycobacterium fortuitum DNA is:

SEQ ID:NO:61 5'-GAGCAGATCG CTGCCACCGC CGGTATCTCC-3' (77° C.).

A useful capture probe for the detection of the thymidine kinase gene of herpes simple virus 1 (HSV-1) DNA is as follows:

SEQ ID:NO:65 5'-AAAGACAGAA TAAAACGCAC GGGTGTTGGG TCG-3' (70.2° C.).

Probes useful for the detection or capture of additional target nucleic acids would be readily apparent to one skilled in the art if the targeted nucleic acid sequences are known. Many such sequences are known in the literature. Thus, the practice of this invention is adequately enabled by knowing those sequences and following the representative teaching herein regarding primers and probes actually shown. Presently, unknown target nucleic acids will also be similarly amplified and detected because this technology could predictably be used in a similar fashion. Potential probes can be screened to see if they have the requisite $T_m$ as defined above. Such probes can be prepared using the same procedures and starting reagents described for primers above.

Additional PCR reagents necessary for PCR include a thermostable DNA polymerase, a DNA polymerase cofactor and appropriate dNTP's. These reagents can be provided individually, as part of a test kit, in reagent chambers of a test device, or in the composition of this invention.

A thermostable DNA polymerase is an enzyme which will add deoxynucleoside monophosphate molecules to the 3' hydroxy end of the primer in a complex of primer and template, but this addition is in a template dependent manner (that is, dependent upon the specific nucleotides in the template). Synthesis of extension products proceeds in the 5' to 3' direction of the newly synthesized strand (or in the 3' to 5' direction of the template) until synthesis is terminated.

The DNA polymerase is "thermostable" meaning that it is stable to heat and preferentially active at higher temperatures, especially the high temperatures used for priming and extension of DNA strands. More particularly, the thermostable DNA polymerases are not substantially inactivated at the high temperatures used in polymerase chain reactions as described herein. Such temperatures will vary depending upon a number of reaction conditions, including pH, the nucleotide composition of the target nucleic acid and primers, the length of primer, salt concentration and other conditions known in the art and will be in the ranges noted below.

A number of thermostable DNA polymerases have been reported in the art, including those mentioned in detail in U.S. Pat. No. 4,965,188 and U.S. Pat. No. 4,889,818 (Gelfand et al), both incorporated herein by reference. Particularly useful polymerases are those obtained from various *Thermus bacterial* species, such as *Thermus aquaticus, Thermus thermophilus, Thermus filiformis* or *Thermus flavus*. Other useful thermostable polymerases are obtained from a variety of other microbial sources including *Thermococcus literalis, Pyrococcus furiosus,* Thermotoga sp. and those described in WO-A-89/06691 (published Jul. 27, 1989). Some useful polymerases are commercially available. A number of techniques are known for isolating naturally-occurring polymerases from organisms, and for producing genetically engineered enzymes using recombinant techniques, as noted in the art cited in this paragraph and as described in EP-A-0 482 714 (published Apr. 29, 1992).

A DNA polymerase cofactor refers to a nonprotein compound on which the enzyme depends for activity. Thus, the enzyme is catalytically inactive without the presence of the cofactor. A number of such materials are known cofactors including manganese and magnesium compounds. Such compounds contain the manganese or magnesium in such a form that divalent cations are released into an aqueous solution. Useful cofactors include, but are not limited to, manganese and magnesium salts, such as chlorides, sulfates, acetates and fatty acid salts (for example, butyric, caproic, caprylic, capric and lauric acid salts). The smaller salts, that is chlorides, sulfates and acetates, are preferred.

Magnesium salts, such as magnesium chlorides and sulfates are most preferred in the practice of the invention.

Also needed for PCR is a deoxyribonucleoside-5'-triphosphate (a dNTP), such as dATP, dCTP, dGTP, dTTP or dUTP. Analogues such as dITP and 7-deaza-dGTP are also useful. The preferred materials, dATP, dCTP, dGTP and dTTP, are used collectively in the assays.

The PCR reagents described herein are provided and used in PCR in any concentration suitable for a given process. The minimal amounts of primers, thermostable DNA polymerase, cofactors and deoxyribonucleotide-5'-triphosphates needed for amplification and suitable ranges of each are well known in the art. Preferably, from about 0.1 to about 50 units of thermostable DNA polymerase per 100 μl of reaction mixture are used for PCR, depending upon the particular activity of a given enzyme. A "unit" is defined herein as the amount of enzyme activity required to incorporate 10 nmoles of total nucleotides (dNTP's) into an extending nucleic acid chain in 30 minutes at 74° C. More preferably, from about 10 to about 25 units of DNA polymerase/100 μl of solution are used. The amount of primer is at least about 0.075 μmolar with from about 0.1 to about 2 μmolar being preferred, but other amounts are well known in the art. The cofactor is generally present in an amount of from about 2 to about 15 mmolar. Each dNTP is present at from about 0.25 to about 3.5 mmolar (about 1 to about 14 mmolar for total of four common dNTP's).

The aqueous composition of this invention is buffered to a pH of from about 7 to about 9 (preferably from about 8 to about 8.5) using one or more suitable buffers including, but not limited to, tris(hydroxymethyl)aminomethane (or salts thereof) and others readily apparent to one skilled in the art.

A particularly useful composition of this invention is a buffered mixture of the primers noted herein, a magnesium cofactor as noted above, each of dATP, dCTP, dGTP and dTTP as noted above, gelatin or a similar hydrophilic colloidal material (in an amount of at least about 5%, by weight), and an alkali metal salt (such as sodium chloride or potassium chloride) present in an amount of from about 10 to about 100 mmolar. More preferably, this composition also includes an appropriate amount of a thermostable DNA polymerase (as described above), and a monoclonal antibody to such DNA polymerase, which antibody inhibits its enzymatic activity at temperatures below about 50° C., but which antibody is deactivated at higher temperatures. Representative monoclonal antibodies are described in U.S. Ser. No. 07/958,144 (filed Oct. 7, 1992 by Scalice et al). Two such monoclonal antibodies are readily obtained by a skilled artisan using conventional procedures, and starting materials including either of hybridoma cell lines HB 11126 and 11127 deposited with the American Type Culture Collection (Rockville, Md.). The monoclonal antibody is present in an amount of from about 5:1 to 500:1 molar ratio to the DNA polymerase (preferably from 25:1 to 100:1 molar ratio).

One preferred composition of this invention is shown in Example 1 below.

In one embodiment of this invention, a method for preparing a reaction mixture for polymerase chain reaction of two or more target DNA's comprises:

A) choosing a set of primers for each distinct target DNA, the primers in each set chosen to be specific to and hybridizable with nucleic acid sequences which are in opposing strands of a distinct target DNA and which are separated from each other along the opposing strands of the distinct target DNA by from 90 to 400 nucleotides each of the primers in each primer set having a $T_m$ within the range of from about 65° to about 74° C., all of the primer $T_m$'s being within about 5° C. of each other, and the primers in each set having nucleotide lengths which differ from each other by no more than 5 nucleotides, the $T_m$'s being calculated using the formula:

$$T_m(°C.)=67.5+0.34(\%G+C)-395/N$$

wherein G and C represent the number of guanine and cytosine nucleotides, respectively, and N represents the total number of nucleotides, and B) mixing the sets of primers chosen in step A) with:

a thermostable DNA polymerase in an amount of from about 0.1 to about 50 units/100 $\mu$l, a DNA polymerase cofactor in an amount of from about 2 to about 15 mmolar, and each of dATP, dCTP, dGTP and dTTP present in an amount of from about 0.25 to about 3.5 mmolar, wherein each of the primers is present in the mixture at a concentration of at least about 0.075 $\mu$molar.

A target nucleic acid can be obtained from any of a variety of sources as noted above, such as a whole blood sample. Generally, it is extracted in some manner to make it available for contact with the primers and other PCR reagents. This usually means removing unwanted proteins and cellular matter from the specimen in a suitable manner. Various procedures are known in the art, including those described by Laure et al in *The Lancet*, pp. 538–540 (Sep. 3, 1988), Maniatis et al, *Molecular Cloning: A Laboratory Manual*, pp. 280–281 (1982), Gross-Belland et al in *Eur.J.Biochem.*, 36, 32 (1973) and U.S. Pat. No. 4,965,188. Extraction of DNA from whole blood or components thereof are described, for example, in EP-A-0 393 744 (published Oct. 24, 1990), Bell et al, *Proc. Natl. Acad. Sci. USA*, 78(9), pp. 5759–5763 (1981) and Saiki et al, *Bio/Technology*, 3, pp. 1008–1012 (1985).

Since the nucleic acid to be amplified and detected is usually in double stranded form, the two strands must be separated (that is, denatured) before priming can take place. This can occur during the extraction process, or be a separate step afterwards. Denaturation is accomplished using a heat treatment alone or in combination with any suitable other physical, chemical or enzymatic means as described in the art. Initial denaturation is generally carried out by heating the specimen suspected of containing the targeted nucleic acid at a first temperature of from about 85° to about 100° C. for a suitable time, for example from about 1 second to 3 minutes.

The denatured strands are then cooled to a temperature which is generally in the range of from about 55° to about 70° C. for priming the strands. The time needed for cooling the denatured strands will vary depending upon the type of apparatus used for the PCR process.

Once the denatured strands are cooled to the second temperature, the reaction mixture containing PCR reagents is incubated at a suitable temperature to effect formation of primer extension products. Generally, this temperature is at least about 50° C., and preferably in the range of from about 62° to about 75° C. The time for incubation can vary widely depending upon the incubation temperature and the length of extension products desired, but in preferred embodiments, it is from about 1 to about 120 seconds. Each cycle of PCR can be carried out using either two or three different temperatures, one for denaturation, and a second and/or third temperature for priming and/or primer extension product formation. That is, some PCR processes utilize a second temperature for priming and a third temperature for primer extension. Preferably, in the practice of this invention, the same temperature is used for both priming and primer extension.

If the hybridized primer extension products are then denatured, PCR can be carried out further in as many cycles of priming, extension and denaturation as desired. Generally, at least 20 cycles will be carried out, with from 20 to 50 cycles being preferred.

The amplification method of this invention is preferably conducted in a continuous, automated manner so that the reaction mixture is temperature cycled in a controlled manner for desired preset times. A number of instruments have been developed for this purpose, as one of ordinary skill in the art would know.

One such instrument for this purpose is described in some detail in U.S. Pat. No. 4,965,188 and EP-A-0 236 069. Generally, this instrument includes a heat conducting container for holding a number of reaction tubes containing reaction mixture, a means for heating, cooling and temperature maintenance, and a computing means to generate signals to control the amplification process, changes in temperature and timing.

A preferred instrument for processing amplification reactions in a disposable chemical test pack is described in some detail in U.S. Pat. No. 5,089,233 (Devaney et al), incorporated herein by reference. In general, this instrument comprises a surface for supporting one or more chemical test packs, pressure applicators supported above the surface for acting on the reaction pack to transfer fluids between adjacent chambers in the test pack, and means for operating the pressure applicators through a range of movements extending across the test pack.

EP-A-0 402 994 provides details of useful chemical test packs which can be processed using the instrument described in U.S. Pat. No. 5,089,233 (noted above). Also described therein are means for heating and cooling the test pack at repeated intervals (that is, through cycles) appropriate for the method of the present invention.

Further details regarding useful PCR processing equipment can be obtained from the considerable literature in this field, and would be readily ascertained by one skilled in the art.

It is also useful for the method of this invention to be carried out in a suitable container. The most crude container would be a test tube, cuvette, flask or beaker, but more sophisticated containers have been fashioned in order to facilitate automated procedures for performing the method (see for example, WO-A-91/12342). For example, cuvette and chemical test packs (also known as pouches), constructed to provide certain temperature characteristics during the practice of the method, are described in U.S. Pat. No. 4,902,624 (Columbus et al), U.S. Pat. No. 5,173,260 (Zander et al) and recently allowed U.S. Ser. No. 07/962,159 (filed Oct. 15, 1992 by Schnipelsky et al), all incorporated herein by reference. Such test packs have a multiplicity of reagent chambers having various reagents, buffers and other materials which are useful at various stages in the amplification or detection method. The aqueous composition of this invention can be incorporated into a reaction chamber for use in PCR. The packs can be appropriately and rapidly heated and cooled in cycles to promote the various steps of the amplification method of this invention. Other useful containers could be suitably fashioned for automated or single use of the method of this invention.

Detection of the amplified target DNA's can be accomplished in a number of known ways, such as those described in U.S. Pat. No. 4,965,188 (noted above). For example, it can be detected using Southern blotting or dot blot techniques. Alternatively, amplification can be carried out using primers that are appropriately labeled (such as with a radioisotope), and the amplified primer extension products are detected using procedures and equipment for detection of radioisotopic emissions.

In one embodiment, the amplified target nucleic acid is detected using an oligonucleotide probe which is labeled for detection and can be directly or indirectly hybridized with one of the primer extension products. Procedures for attaching labels and preparing probes are well known in the art, for example, as described by Agrawal et al, *Nucleic Acid Res.*, 14, pp. 6227–45 (1986), U.S. Pat. No. 4,914,210 (Levenson et al) relating to biotin labels, U.S. Pat. No. 4,962,029 (Levenson et al) relating to enzyme labels, and the references noted therein. Useful labels include radioisotopes, electron-dense reagents, chromogens, fluorogens, phosphorescent moieties, ferritin and other magnetic particles (see U.S. Pat. No. 4,795,698 issued to Owen et al and U.S. Pat. No. 4,920,061 issued to Poynton et al), chemiluminescent moieties and enzymes (which are preferred). Useful enzymes include, glucose oxidase, peroxidases, uricase, alkaline phosphatase and others known in the art and can be attached to oligonucleotides using known procedures. Substrate reagents which provide a chemiluminescent or calorimetric signal in the presence of a particular enzyme label would be readily apparent to one skilled in the art.

Where the label is a preferred enzyme such as a peroxidase, at some point in the assay, hydrogen peroxide and a suitable dye-forming composition are added to provide a detectable dye (that is, a colorimetric signal). For example, useful dye-providing reagents include tetramethylbenzidine and derivatives thereof, and leuco dyes, such as triarylimidazole leuco dyes (as described in U.S. Pat. No. 4,089,747 of Bruschi), or other compounds which react to provide a dye in the presence of peroxidase and an oxidant such as hydrogen peroxide. Particularly useful dye-providing compositions are described in U.S. Pat. No. 5,024,935 (McClune et al), incorporated herein by reference. Chemiluminescent signals can be generated using acridinium salts or luminol and similar compounds in combination with enhancers in the presence of peroxidase.

Detection of the presence of the probe which is in the complementary product can be achieved using suitable detection equipment and procedures which are well known. Certain probes may be visible to the eye without the use of detection equipment.

In a preferred embodiment, one or both of the primers in each primer set used to detect a target nucleic acid is labeled with a specific binding moiety. The specific binding moiety can be the same or different for each set of primers. Such labels include any molecule for which there is a receptor molecule that reacts specifically with the specific binding moiety. Examples of specific binding pairs (one of which can be the label) include, but are not limited to, avidin/biotin, streptavidin/biotin, sugar/lectin, antibody/hapten, antibody/antigen and others readily apparent to one skilled in the art. The receptor is then conjugated with a detectable label moiety, such as an enzyme using known technology.

Most preferably, one or both primers of each primer set are labeled with biotin (or a equivalent derivative thereof), and the amplified target nucleic acid is detected using a conjugate of avidin (or streptavidin) with an enzyme. The enzyme attached to the specific binding complex is then detected using the appropriate substrate reagents.

In order for the amplified target nucleic acid to be detected, it is often useful (but not necessary) for it to be separated from the other materials in the reaction medium. This is done by any of a number of ways, including using a capture reagent having a capture probe which is covalently attached to a water-insoluble support. The capture probe hybridizes with the amplified target nucleic acid and the captured material can then be separated from unhybridized materials in a suitable manner, such as by filtration, centrifugation, washing or other suitable separation techniques.

Capture probes can be attached to water-insoluble supports using known attachment techniques. One such technique is described in EP-A-0 439 222 (published Sep. 18, 1991). Other techniques are described for example in U.S. Pat. No. 4,713,326 (Dattagupta et al), U.S. Pat. No. 4,914,210 (Levenson et al) and EP-B-0 070 687 (published Jan. 26, 1983). Useful separation means are microporous filtration membranes such as the polyamide membranes marketed by Pall Corp. (for example as LOPRODYNE™ or BIODYNE™ membranes) which can be used to separate captured target nucleic acids from unhybridized materials.

Any useful solid support can be used for separation of water-insoluble product for detection, including a microtiter plate, test tube, beaker, beads, film, membrane filters, filter papers, gels, magnetic particles or glass wool. It can be made of a number of materials including glass, ceramics, metals, naturally occurring or synthetic polymers, cellulosic materials, filter materials and others readily apparent to one of ordinary skill in the art. Particularly useful solid support materials are polymeric or magnetic particles generally having an average particle size of from about 0.001 to about 10 μmeters. Further details about such preferred polymeric particles, including useful monomers, methods of preparing them and attachment of receptor molecules, are provided in U.S. Pat. No. 4,997,772 (Sutton et al), U.S. Pat. No. 5,147,777 (Sutton et al), U.S. Pat. No. 5,155,166 (Danielson et al), all of which are incorporated herein by reference.

The detection can also be carried out by immobilizing a capture probe or capture reagent on a flat substrate, such as the microporous filtration membranes described above, or on thin polymeric films, uncoated papers or polymer coated papers, a number of which are known in the art. Other details about such materials are provided in U.S. Ser. No. 07/571,560 (filed Sep. 4, 1990 as a CIP of U.S. Ser. No. 07/306,954, filed Feb. 3, 1989 by Findlay et al, and corresponding to EP-A-0 408 738, published Jan. 23, 1991).

Particularly useful arrangements of a capture reagent are described, for example, in U.S. Ser. No. 07/837,772 (filed Feb. 18, 1992 by Sutton et al, corresponding to WO 92/16659, published Oct. 1, 1992) and U.S. Pat. No. 5,173,260 (noted above). The capture probes are covalently attached (either directly or through chemical linking groups) to the same type of polymeric particles, and the resulting capture reagents are immobilized on a heat or ultrasonic sealable support (for example, a sheet, membrane, fibrous mat, film). One particularly useful sealable support is a laminate of polyethylene and a polyester such as polyethylene terephthalate. The capture reagents can be disposed in distinct regions on the water-insoluble support which is part of a suitable test device (as described above). Such test devices can also be defined as diagnostic elements. For example, the support can have disposed thereon a plurality of stripes or spots of various capture reagents. The multiplicity of capture probes arranged in defined regions on such supports all have the $T_m$ values as described above, that is the $T_m$ values differ by no more than about 15° C. (preferably by no more than about 5° C.).

Thus, according to one embodiment of this invention, a diagnostic element comprises a water-insoluble, heat or ultrasonic sealable support, having disposed thereon in distinct regions thereof, a plurality (two or more) of capture reagents, each of the capture reagents having a capture probe specific for and hybridizable with a distinct (that is, unique to that capture probe) target DNA associated with an infectious agent at a temperature of from about 40° to about 55° C., each of the capture probes having from 10 to 40 nucleotides and a $T_m$ greater than about 50° C., and the $T_m$'s of all capture probes differing by no more than about 15° C. The present invention includes diagnostic test kits which can include the composition of this invention, an additional PCR reagent and other materials, equipment and instructions needed to carry out the method of the invention. The kits can include one or more detection or capture probes, multiple primer sets and test devices for the assays. In some embodiments, the kit components are separately packaged for use in a suitable container or test device. In other embodiments, the kit contains a test device having within separate compartments, some or all of the reagents and compositions needed for the assay. In such embodiments, the separate packaging of the kit components can be within a single test device.

The following examples are included to illustrate the practice of this invention, and are not meant to be limiting in any way. All percentages are by weight unless otherwise noted.

MATERIALS AND METHODS FOR EXAMPLES

Recombinant DNA polymerase from *Thermus aquaticus* was prepared using known procedures, such as that described in EP-A-0 482 714 (noted above) and had an activity of about 250,000 units/mg of protein.

The primers and probes were prepared using known starting materials and procedures using an Applied Biosystems Model 380B, three column DNA synthesizer using standard phosphoramidite chemistry and the ABI 1 μmolar scale, fast cycle protocol. Nucleoside-3'-phosphoramidites and nucleoside derivatized controlled pore glass supports were obtained from Applied Biosystems. The primers had the sequences identified above. They were functionalized at the 5' end with two tetraethylene glycol spacers followed by a single commercially available DuPont biotin phosphoramidite. The probes were functionalized at the 3' end with two tetraethylene glycol spacers followed by a single aminodiol linking group according to U.S. Pat. No. 4,914,210 (noted above). All purifications were carried out using a nucleic acid purification column, followed by reversed phase HPLC techniques.

The novel oligonucleotides of this invention having the sequences:
SEQ ID:NO:26 5'-GAGATGGGAA TCCATATGCT GTATGTGAT-3',
SEQ ID:NO:27 5'-GGACACAGTG GCTTTTGACA GTTAATACA-3',
SEQ ID:NO:28 5'-GATGGTCCAG CTGGACAAGC AGAAC-3',
SEQ ID:NO:29 5'-CCTAGTGTGC CCATTAACAG GTCTTC-3',
SEQ ID:NO:30 5'-GACACAGAAA ATGCTAGTGC TTATGCAGC-3',
SEQ ID:NO:31 5'-GGTGGACAAT CACCTGGATT TACTGCAAC-3',
SEQ ID:NO:32 5'-CCTGATCTGT GCACGGAACT GAACACT-3',
SEQ ID:NO:33 5'-CCCAGTGTTA GTTAGTTTTT CCAATGTGTC TG-3',
SEQ ID:NO:34 5'-TGCCTGCGGT GCCAGAAACC GTTGAAT-3',
SEQ ID:NO:35 5'-TGCTCGGTTG CAGCACGAAT GGCACT-3',
SEQ ID:NO:36 5'-GAGCCGAACC ACAACGTCAC ACAATGTT-3',
SEQ ID:NO:37 5'-GGACACACAA AGGACAGGGT GTTCAGAAA-3',
SEQ ID:NO:39 5'-GCGACTCAGA GGAAGAAAAC GATG-3',
SEQ ID:NO:40 5'-GAGATCGAGC TGGAGGATCC GTACG-3',
SEQ ID:NO:41 5'-AGCTGCAGCC CAAAGGTGTT GGACT-3',
SEQ ID:NO:51 5'-GGAACAACAT TAGAACAGCA ATACAACAAA CCG-3',
SEQ ID:NO:52 5'-AATATTGTAA CCTTTTGTTG CAAGTGTGAC TC-3',
SEQ ID:NO:53 5'-CCTATAGGTG GTTTGCAACC AATTAAACAC-3',
SEQ ID:NO:54 5'-GAGGTATTTG AATTTGCATT TAAAGATTTA TTTGT-3',
SEQ ID:NO:55 5'-GCAAGACAGT ATTGGAACTT ACAGAGG-3',
SEQ ID:NO:56 5'-GTGTTGTAAG TGTGAAGCCA GATTTGA-3',
SEQ ID:NO:57 5'-GAGCAGATTG CGGCCACCGC AGCGATTTCG-3',
SEQ ID:NO:63 5'-CCGGGAGATG GGGGAGGCTA ACTGA-3',
SEQ ID:NO:64 5'-GGGGTGGGGA AAAGGAAGAA ACGCG-3', and
SEQ ID:NO:65 5'-AAAGACAGAA TAAAACGCAC GGGTGTTGGG TCG-3',
were prepared using the procedures just described.

Deoxyribonucleotides (dNTP's) were obtained from Sigma Chemical Co.

The monoclonal antibody specific to the noted DNA polymerase was prepared as described in U.S. Ser. No. 07/958,144 (filed Oct. 7, 1992 by Scalice et al). Generally, it was prepared from the immune cells of DNA polymerase immunized mice using conventional procedures, such as those described by Milstein et al, *Nature* 256, pp. 495–497, 1975 and hybridoma cell lines (either HB 11126 or 11127 from ATCC), whereby antibody secreting cells of the host animal were isolated from lymphoid tissue (such as the spleen) and fused with SP2/0-Ag14 murine myeloma cells in the presence of polyethylene glycol, diluted into selective media and plated in multiwell tissue culture dishes. About 7–14 days later, the hybridoma cells containing the antibodies were harvested, and purified using conventional techniques.

An avidin-peroxidase conjugate solution comprised a commercially available (Zymed Laboratories, Inc.) conjugate of avidin and horseradish peroxidase (126 μl/l), casein (0.5%) and merthiolate (0.5%).

A wash solution (pH 7.4) contained sodium phosphate, monobasic 1-hydrate (25 mmolar), sodium chloride (373 mmolar), (ethylenedinitrilo)tetracetic acid disodium salt (2.5 mmolar), ethylmercurithiosalicylic acid sodium salt (25 μmolar), and decyl sodium sulfate (38 mmolar).

The dye-providing composition (pH 6.8) contained 4,5-bis(4-dimethylaminophenyl)-2-(4-hydroxy-3-methoxyphenyl)imidazole (250 μmolar), poly(vinyl pyrrolidone) (112 mmolar), agarose (0.5%), diethylenetri-aminepentaacetic acid (100 μmolar), 4'-hydroxyacetanilide (5 mmolar) and sodium phosphate, monobasic, 1-hydrate (10 mmolar).

HIV-I DNA was extracted from the HUT/AAV 78 cell line using conventional procedures, and following cell lysis and protein digestion, was purified by phenol/chloroform extraction: tris-saturated phenol (750 μl) was added to the cell suspension, and phenol/lysate solutions were mixed and separated by centrifugation. The aqueous phase was then transferred into a fresh 2 ml tube. This procedure was repeated using chloroform isoamyl alcohol. The aqueous layer was brought to 0.3 molar sodium acetate. Nucleic acids were precipitated by adding 95% cold ethanol and storing at −70° C. for 1 hour. The concentration of HIV-I DNA was then determined at $A_{260}$ and serial dilutions of varying copy number were made in TE buffer [tris(hydroxymethyl) aminomethane (1 mmolar) and (ethylenedinitrilo)tetraacetic acid (0.1 mmolar)] for experimental use. A sample (10 μl) of the diluted solutions was added to each PCR reaction mixture (300 μl).

Pure hCMV DNA was obtained by purifying commercially available crude hCMV DNA (Advanced Biotech's strain AD169) using a conventional sucrose gradient and phenol/chloroform extraction procedures. The concentration of hCMV DNA was then determined at $A_{260}$ and target dilutions of varying calculations of copy number were made for experimental use in TE buffer [tris(hydroxymethyl) aminomethane (1 mmolar), ethylenediaminetetraacetic acid (0.1 mmolar)]. A sample (10 μl) of the diluted solutions were added to 300 μl of PCR reaction mixture.

Two "nonsense" probes were used as control reagents for the assays to amplify and detect HIV-I DNA and had the sequences:
SEQ ID:NO:8
5'-GGTGTCACCC CCAGAGTCCC CTGTACCCGC-3'
SEQ ID:NO:9
5'-ATCCTGGGAT TAAATAAAAT AGTAAGAATG TATAGCCCTA C-3'

The same "nonsense" probes were used as controls for the hCMV DNA assays also.

Capture reagents were prepared by attaching the capture probes identified above to particles of poly[styrene-co-3-(p-vinylbenzylthio)propionic acid] (95:5 molar ratio, 1 μm average diameter) in the following manner. A suspension of the particles in water was washed twice with 2-(N-morpholino)ethanesulfonic acid buffer (0.1 molar, pH 6). and suspended to approximately 10% solids. A sample (3.3 ml) of the washed particles, diluted to 3.33% solids in the buffer (0.1 molar), was mixed with 1-(3-dimethylaminopropyl)-3-ethylcarbodiimide hydrochloride (2.1 ml of 84 mg/ml water) and the appropriate probe (983 μl of 44.44 OD/ml nanopure water). The resulting suspension was heated at 50° C. in a water bath for about two hours with intermittent mixing and centrifuged. The particles were washed three times with tris(hydroxy-methyl) aminomethane buffer (0.01 molar, pH 8) containing (ethylenedinitrilo)tetraacetic acid disodium salt (0.0001 molar) and resuspended therein to 4% solids.

Capture probes used for the detection of amplified HIV-I DNA were SEQ ID:NO:6 and SEQ ID:NO:7, with the first one being for the "gag" region of HIV-I DNA and the second one for the "env" region of HIV-I DNA.

Control capture reagents were similarly prepared using the "nonsense" probes identified above.

All of the capture reagents were mounted on a heat sealable polyethylene/polyester laminate (treated by corona discharge) in test devices prepared as described in WO-A-92/16659 (noted above) so that the assay fluids and reagents contacted all of the capture reagents at about the same time. PCR was carried out using an automated Kodak PCR processor which is described in detail in U.S. Pat. No. 5,089,233, which is incorporated herein by reference.

Primers (and $T_m$) used for the amplification and detection of hCMV DNA were as follows:
SEQ ID:NO:10 5'-TGCACTGCCA GGTGCTCGG CTCAT-3' (72.1° C.), and
SEQ ID:NO:11 5'-CACCACGCAG CGGCCCTTGA TGTTT-3' (72.1° C.).

A capture reagent for hCMV DNA was prepared as described above using the following capture probe ($T_m$):
SEQ ID:NO:12 5'-GAACCGAGGG CCGGCTCACC TCTATGTTGG-3' (75.8° C.).

Other reagents and materials were obtained either from commercial sources or prepared using readily available starting materials and conventional procedures.

The following examples are included to illustrate the practice of this invention, and are not meant to be limiting in any way. All percentages are by weight unless otherwise indicated.

EXAMPLE 1

Buffered Composition Containing HIV-I DNA Primers

One preferred composition of this invention was prepared by mixing primers with additional PCR reagents. This composition contained tris(hydroxymethyl)aminomethane hydrochloride buffer (10 mmolar, pH 8), tris (hydroxymethyl)aminomethane buffer (6.86 mmolar), potassium chloride (50 mmolar), ethylenediaminetetraacetic acid (686 μmolar), magnesium chloride (10 mmolar), gelatin (100 μg/ml), dATP, dCTP, dGTP and dTTP (1.5 mmolar of each), glycerol (9.5%), primers (0.4 μmolar of each), DNA polymerase identified above (48 units/300 μl), and a monoclonal antibody specific to DNA polymerase identified above (50:1 molar ratio to DNA polymerase). The primers included were those identified as SEQ ID:NO:1 and SEQ ID:NO:5 which are specific to nucleic acid sequences in the "gag" region of HIV-I DNA, and SEQ ID:NO:3 and SEQ ID:NO:4 which are specific to nucleic acid sequences in the "env" region of HIV-I DNA. The composition also contained phenol/chloroform purified CEM cells (normal uninfected lymphocytes, at either 2.75 or 6 μg/300 μl) to simulate a human blood sample.

EXAMPLE 2

Simultaneous Amplification and Detection of HIV-I DNA and hCMV DNA

This example demonstrates the practice of the present invention using the composition described in Example 1 to simultaneously detect HIV-I DNA along with hCMV DNA, except that the composition further contained 0.4 μmolar of each of the primers identified above as SEQ ID:NO:10 and SEQ ID:NO:11.

Twenty-four assays were carried out to detect the following various concentrations of the target nucleic acids in the test samples having two different amounts of CEM cells:

Sample a) 20,000 copies of hCMV DNA and 20,000 copies of HIV-I DNA,

Sample b) 500 copies of hCMV DNA and 500 copies of HIV-I DNA,

Sample c) 100 copies of hCMV DNA and 100 copies of HIV-I DNA,

Sample d) 100 copies of hCMV DNA and 20,000 copies of HIV-I DNA,

Sample e) 20,000 copies of hCMV DNA and 100 copies of HIV-I DNA, and

Sample f) 100 copies of hCMV DNA and 500 copies of HIV-I DNA.

In these assays, a nucleic acid sequence in the "late antigen" region of hCMV DNA was detected, and nucleic acid sequences in the "gag" and "env" regions of HIV-I DNA were detected. Two replicates were carried out for each assay.

The amplification and detection procedure for the assays were as follows:

Amplification:
Denature by heating at 95° C. for 60 seconds,
40 cycles of priming and extending at 68° C. for 30 seconds, and heating at 94° C. for 15 seconds.

Detection:
Denature the amplified strands at 97° C. for 120 seconds,
Capture the amplified products with the capture reagents at 50° C. for 5 minutes,
Contact and incubate the captured products with the avidin-peroxidase conjugate solution at 40° C. for 1 minute,
Wash the captured products using the wash solution at 40° C. for 1 minute,
Add the dye-providing composition and incubate at 40° C. for 2 minutes, and
Read the dye signal.

The results of the assays (two replicates of each assay) of Samples a)–f), are shown in the bar graphs of FIGS. 1–6, respectively, where the dye signal is shown in the y-axis (where "0" represents no dye signal, and "10" represents highest dye density). In each figure, the first set of bar graphs are assays whereby 2.75 µg CEM cells were present, and the second set of bar graphs are assays whereby 6 µg CEM cells were present. Also, in all figures, the first bar (identified as "1") in each set of bars represents the signal from hCMV DNA ("late antigen" region), the second bar (identified as "2") represents the signal from HIV-I DNA ("gag" region), and the third bar (identified as "3") represents the signal from HIV-I DNA ("env" region). The dye signals for both Control capture reagents were essentially zero, so they are not illustrated on the bar graphs.

EXAMPLE 3

Amplification and Detection of HIV-I DNA Alone

This example was carried out similarly to Example 2 for the amplification and detection of two nucleic acid sequences of HIV-I DNA ("gag" and "env" regions) only in Samples a)–f) using the composition of Example 1 (6 µg CEM cells only).

Figure 7:
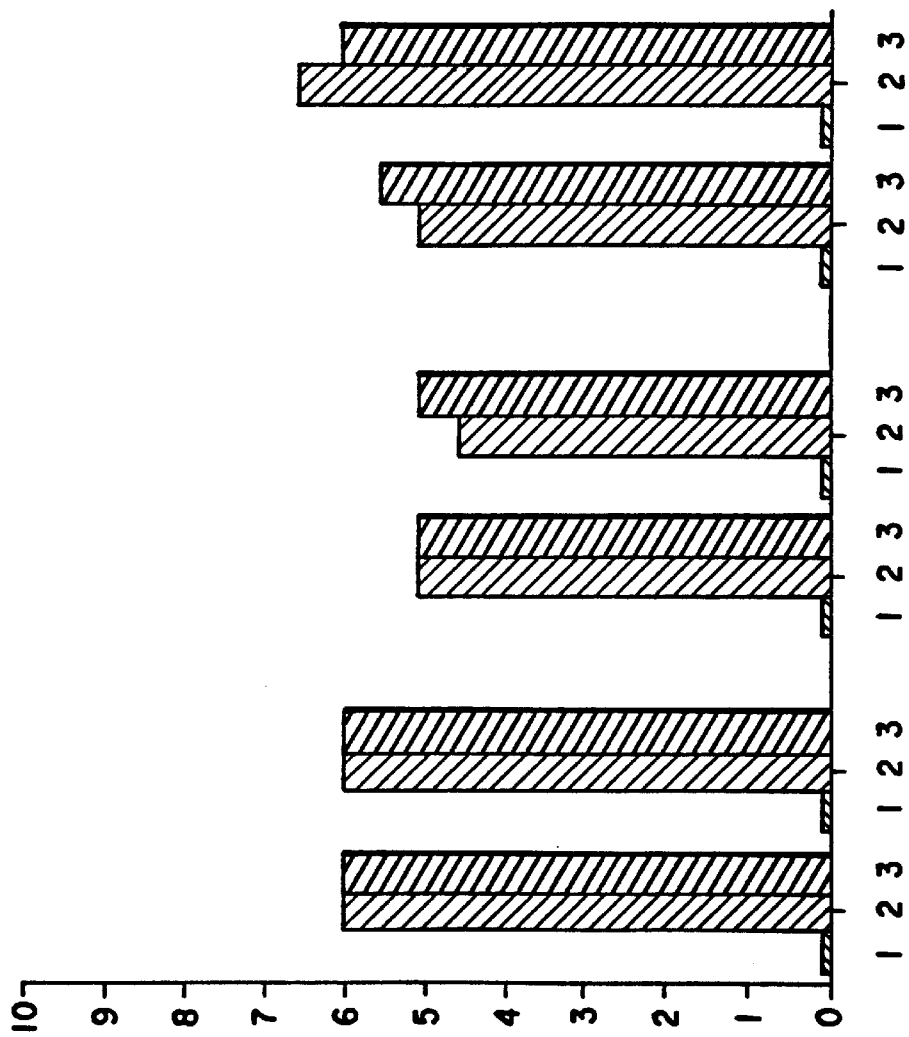
FIGS. 7 and 8 are sets of bar graphs showing dye signals for replicate PCR assays of various concentrations of HIV-I DNA, as described in Example 3 below.
Figure 8:
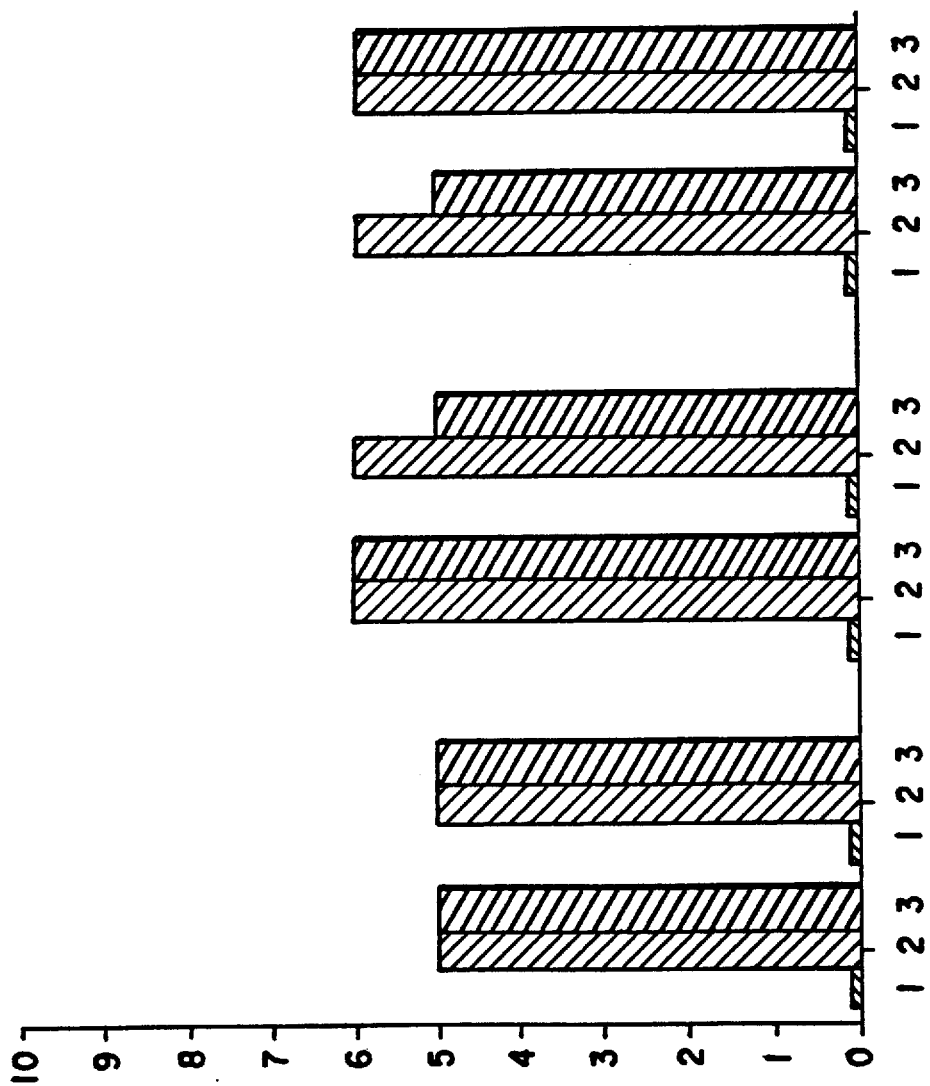

FIG. 7 shows the dye signal results of the PCR process for the two replicates of each of Samples a)–c), and FIG. 8 shows the dye signal results of the PCR process for the replicates of each of Samples d)–f). Clear signals were observed for the presence of HIV-I DNA (bars identified as "2" and "3"). Small background signals were also observed (bar identified as "1" in each set of bar graphs).

EXAMPLE 4

Buffered Composition Containing hCMV DNA Primers

Another preferred composition of this invention was prepared by mixing primers with additional PCR reagents. This composition contained tris(hydroxymethyl) aminomethane hydrochloride buffer (10 mmolar, pH 8), potassium chloride (50 mmolar), magnesium chloride (10 mmolar), gelatin (100 µg/ml), dATP, dCTP, dGTP and dTTP (1.5 mmolar of each), glycerol (7.5%), primers (0.4 µmolar of each), DNA polymerase identified above (48 units/300 µl), and a monoclonal antibody specific to DNA polymerase identified above (50:1 molar ratio to DNA polymerase). The primers included were those identified as SEQ ID:NO:10 and 11 which are specific to nucleic acid sequences of hCMV DNA. The composition also contained phenol/chloroform purified CEM cells (normal uninfected lymphocytes, at either 2.75 or 6 µg/300 µl) to simulate a human blood sample.

EXAMPLE 5

Amplification and Detection of hCMV DNA Alone

This example was carried out similarly to Example 2 for the amplification and detection of hCMV DNA ("late antigen" region only) in Samples a)–f) using the composition of Example 4 (2.75 µg CEM cells only).

Figure 9:
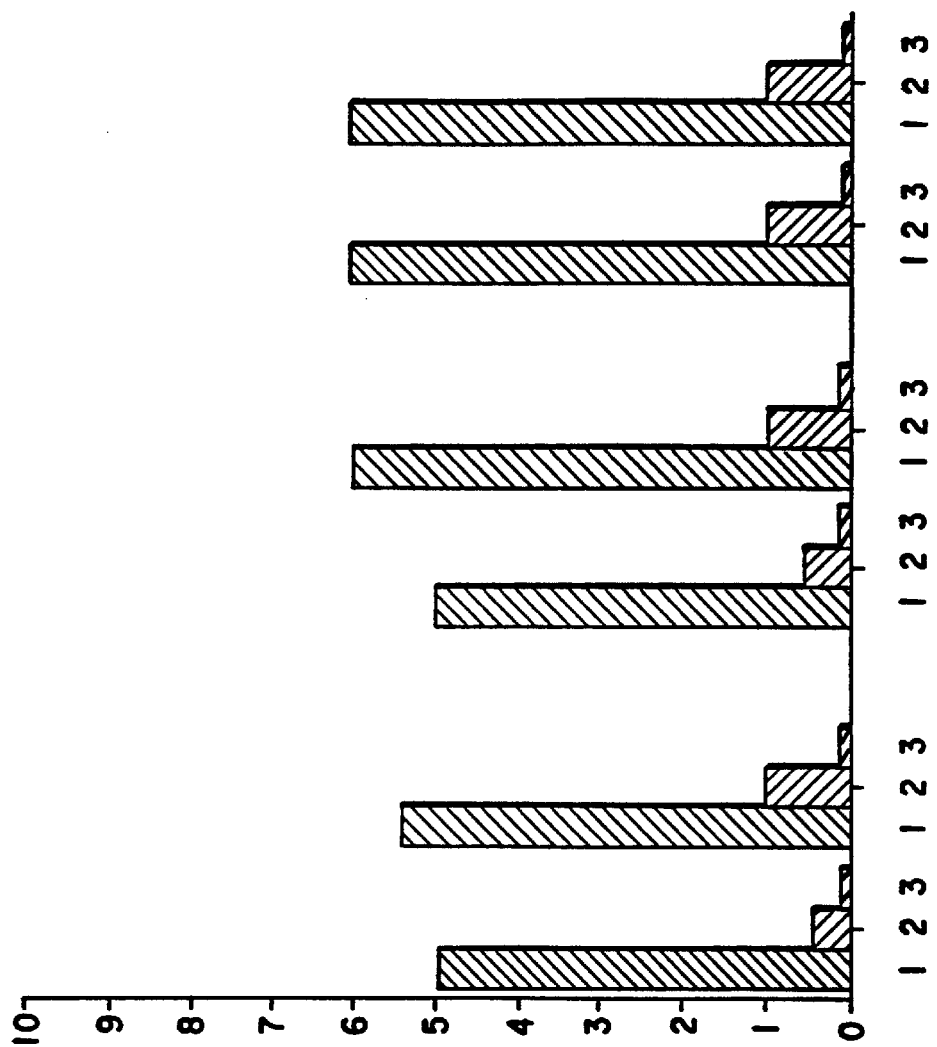
FIGS. 9 and 10 are sets of bar graphs showing dye signals for replicated PCR assays of various concentrations of hCMV DNA, as described in Example 5 below.
Figure 10:
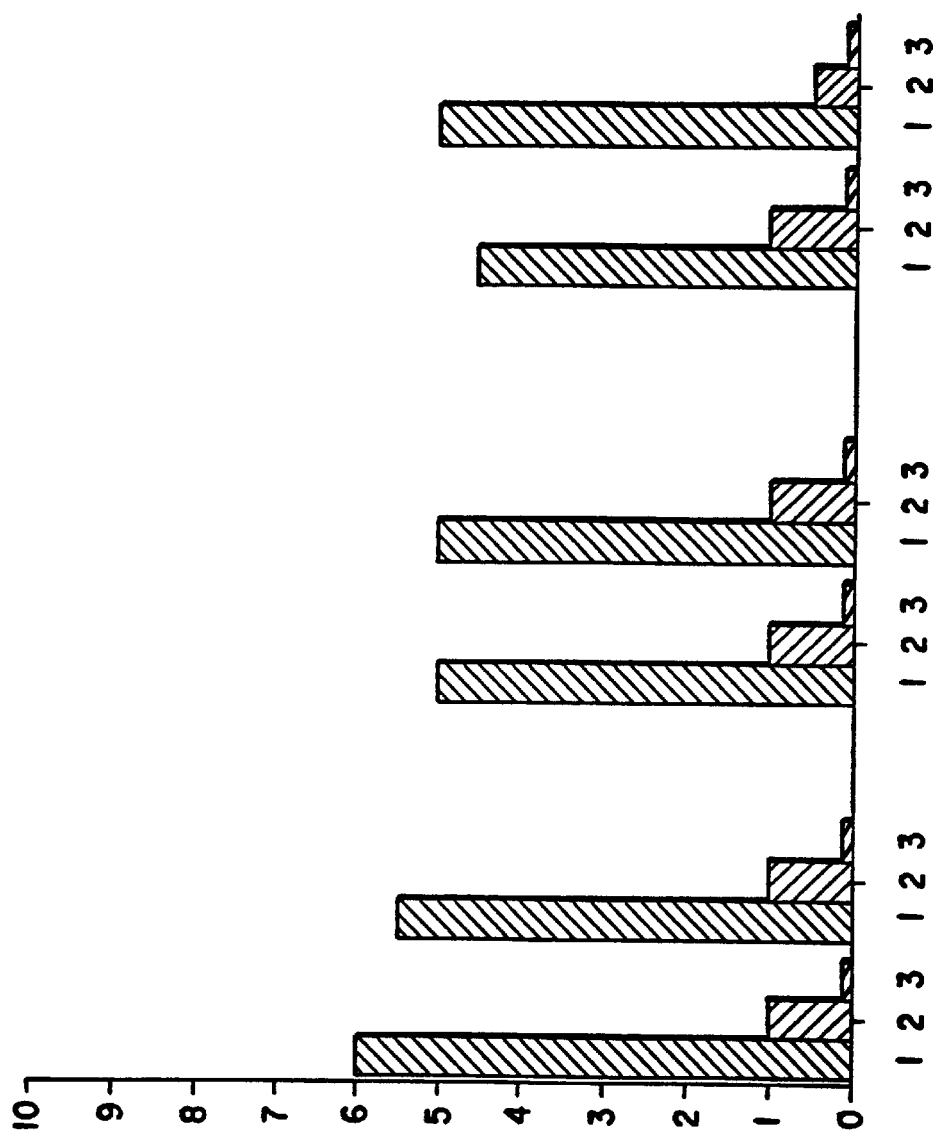

FIG. 9 shows the dye signal results of the PCR process for the two replicates of each of Samples a)–c), and FIG. 10 shows the dye signal results of the PCR process for the replicates of each of Samples d)–f). Clear signals were observed for the presence of hCMV DNA (bar graphs labeled "1"). Small background signals were also observed (labeled as "2" and "3", respectively in each set of bar graphs) from the presence of HIV-I DNA ("gag" and "env" regions).

The invention has been described in detail with particular reference to preferred embodiments thereof, but it will be understood that variations and modifications can be effected within the spirit and scope of the invention.

We claim:

1. A diagnostic element comprising a water-insoluble, heat or ultrasonic sealable support, having disposed thereon in distinct regions thereof, a plurality of capture reagents, each of said capture reagents having a capture probe specific for and hybridizable with a distinct target DNA at a temperature of from about 40° to about 55° C., each of said capture probes having from about 10 to 40 nucleotides and a Tm greater than about 50 C, and the Tm's of all capture probes differing by no more than about 15 C; and wherein said diagnostic element further comprises a plurality of primer pairs wherein each member of a pair is specific for and hybridizable with nucleic acid sequences which are in opposing strands of said target DNA's and which are separated by from 90 to 400 nucleotides, and wherein each of said primer pairs is specific for and hybridizable with one of each of said distinct target DNA's, and wherein the Tm's of the primers are within the range of from about 65° to about 74° C., all of the primer Tm's being within about 5° C. of each other, and all of the primers having nucleotide lengths which differ from each other by no more than 5 nucleotides.

* * * * *

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO:1:

AGTGGGGGGA CATCAAGCAG CCATGCAA        28

( 2 ) INFORMATION FOR SEQ ID NO:2:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:2:

TTCCTGCTAT GTCACTTCCC CTTGGTTC        28

( 2 ) INFORMATION FOR SEQ ID NO:3:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:3:

TAGCACCCAC CAGGGCAAAG AGAAGAGT        28

( 2 ) INFORMATION FOR SEQ ID NO:4:

( i ) SEQUENCE CHARACTERISTICS:

( A ) LENGTH: 28 nucleotides
                ( B ) TYPE: Nucleic acid
                ( C ) STRANDEDNESS: Single
                ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:4:

AGATGCTGTT GCGCCTCAAT AGCCCTCA                    28

( 2 ) INFORMATION FOR SEQ ID NO:5:

( i ) SEQUENCE CHARACTERISTICS:
                ( A ) LENGTH: 26 nucleotides
                ( B ) TYPE: Nucleic acid
                ( C ) STRANDEDNESS: Single
                ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:5:

CTTGGTTCTC TCATCTGGCC TGGTGC                      26

( 2 ) INFORMATION FOR SEQ ID NO:6:

( i ) SEQUENCE CHARACTERISTICS:
                ( A ) LENGTH: 28 nucleotides
                ( B ) TYPE: Nucleic acid
                ( C ) STRANDEDNESS: Single
                ( D ) TOPOLOGY: Linear ( i i ) MOLECULE TYPE: Probe for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:6:

GAGACCATCA ATGAGGAAGC TGCAGAAT                    28

( 2 ) INFORMATION FOR SEQ ID NO:7:

( i ) SEQUENCE CHARACTERISTICS:
                ( A ) LENGTH: 28 nucleotides
                ( B ) TYPE: Nucleic acid
                ( C ) STRANDEDNESS: Single
                ( D ) TOPOLOGY: Linear (i i) MOLECULE TYPE: Probe for HIV-I DNA (i i i) HYPOTHETICAL: No (i v) ANTI-SENSE: No (v) ORIGINAL SOURCE: Synthetically prepared (v i i) IMMEDIATE SOURCE: Same (x) PUBLICATION INFORMATION: None (x i) SEQUENCE DESCRIPTION: SEQ ID NO:7:

GTGCAGCAGC AGAACAATTT GCTGAGGG 28

(2) INFORMATION FOR SEQ ID NO:8:

(i) SEQUENCE CHARACTERISTICS:
(A) LENGTH: 30 nucleotidses
(B) TYPE: Nucleic acid
(C) STRANDEDNESS: Single
(D) TOPOLOGY: Linear (i i) MOLECULE TYPE: Nonsense probe (i i i) HYPOTHETICAL: No (i v) ANTI-SENSE: No (v) ORIGINAL SOURCE: Synthetically prepared (v i i) IMMEDIATE SOURCE: Same (x) PUBLICATION INFORMATION: Unknown (x i) SEQUENCE DESCRIPTION: SEQ ID NO:8:

GGTGTCACCC CCAGAGTCCC CTGTACCCGC 30

(2) INFORMATION FOR SEQ ID NO:9:

(i) SEQUENCE CHARACTERISTICS:
(A) LENGTH: 41 nucleotides
(B) TYPE: Nucleic acid
(C) STRANDEDNESS: Single
(D) TOPOLOGY: Linear (i i) MOLECULE TYPE: Oligonucleotide from HIV-I DNA (i i i) HYPOTHETICAL: No (i v) ANTI-SENSE: No (v) ORIGINAL SOURCE: Synthetically prepared (v i i) IMMEDIATE SOURCE: Same (x) PUBLICATION INFORMATION: Unknown (x i) SEQUENCE DESCRIPTION: SEQ ID NO:9:

ATCCTGGGAT TAAATAAAAT AGTAAGAATG TATAGCCCTA C 41

(2) INFORMATION FOR SEQ ID NO:10:

(i) SEQUENCE CHARACTERISTICS:
(A) LENGTH: 25 nucleotides
(B) TYPE: Nucleic acid
(C) STRANDEDNESS: Single
(D) TOPOLOGY: Linear (i i) MOLECULE TYPE: Primer for hCMV DNA (i i i) HYPOTHETICAL: No (i v) ANTI-SENSE: No (v i) ORIGINAL SOURCE: Synthetically prepared (v i i) IMMEDIATE SOURCE: Same (x) PUBLICATION INFORMATION: None (x i) SEQUENCE DESCRIPTION: SEQ ID NO:10:

TGCACTGCCA GGTGCTTCGG CTCAT 25

(2) INFORMATION FOR SEQ ID NO:11:

(i) SEQUENCE CHARACTERISTICS:
        (A) LENGTH: 25 nucleotides
        (B) TYPE: Nucleic acid
        (C) STRANDEDNESS: Single
        (D) TOPOLOGY: Linear (i i) MOLECULE TYPE: Primer for hCMV DNA (i i i) HYPOTHETICAL: No (i v) ANTI-SENSE: No (v i) ORIGINAL SOURCE: Synthetically prepared (v i i) IMMEDIATE SOURCE: Same (x) PUBLICATION INFORMATION: U.S. 5,147,777

(x i) SEQUENCE DESCRIPTION: SEQ ID NO:11:

CACCACGCAG CGGCCCTTGA TGTTT 25

(2) INFORMATION FOR SEQ ID NO:12:

(i) SEQUENCE CHARACTERISTICS:
        (A) LENGTH: 30 nucleotides
        (B) TYPE: Nucleic acid
        (C) STRANDEDNESS: Single
        (D) TOPOLOGY: Linear (i i) MOLECULE TYPE: Probe for hCMV DNA (i i i) HYPOTHETICAL: No (i v) ANTI-SENSE: No (v i) ORIGINAL SOURCE: Synthetically prepared (v i i) IMMEDIATE SOURCE: Same (x) PUBLICATION INFORMATION: U.S. 5,147,777

(x i) SEQUENCE DESCRIPTION: SEQ ID NO:12:

GAACCGAGGG CCGGCTCACC TCTATGTTGG 30

(2) INFORMATION FOR SEQ ID NO:13:

(i) SEQUENCE CHARACTERISTICS:
        (A) LENGTH: 30 nucleotides
        (B) TYPE: Nucleic acid
        (C) STRANDEDNESS: Single
        (D) TOPOLOGY: Linear (i i) MOLECULE TYPE: Primer for HIV-I DNA (i i i) HYPOTHETICAL: No (i v) ANTI-SENSE: No (v i) ORIGINAL SOURCE: Synthetically prepared (v i i) IMMEDIATE SOURCE: Same ( x ) PUBLICATION INFORMATION: None ( x i ) SEQUENCE DESCRIPTION: SEQ ID NO:13:

CCTGCTATGT CACTTCCCCT TGGTTCTCTC 30

( 2 ) INFORMATION FOR SEQ ID NO:14:

( i ) SEQUENCE CHARACTERISTICS:
        ( A ) LENGTH: 27 nucleotides
        ( B ) TYPE: Nucleic acid
        ( C ) STRANDEDNESS: Single
        ( D ) TOPOLOGY: Linear ( i i ) MOLECULE TYPE: Primer for HIV-II DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:14:

AAGTAGACCA ACAGCACCAC CTAGCGG 27

( 2 ) INFORMATION FOR SEQ ID NO:15:

( i ) SEQUENCE CHARACTERISTICS:
        ( A ) LENGTH: 29 nucleotides
        ( B ) TYPE: Nucleic acid
        ( C ) STRANDEDNESS: Single
        ( D ) TOPOLOGY: Linear ( i i ) MOLECULE TYPE: Primer for HIV-II DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:15:

GCAGCCTTCT GAGAGTGCCT GAAATCCTG 29

( 2 ) INFORMATION FOR SEQ ID NO:16:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: Primer for HIV-II DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:16:

GGGATAGTGC AGCAACAGCA ACAGCTGT 28

( 2 ) INFORMATION FOR SEQ ID NO:17:

( i ) SEQUENCE CHARACTERISTICS:
        ( A ) LENGTH: 29 nucleotides
        ( B ) TYPE: Nucleic acid
        ( C ) STRANDEDNESS: Single
        ( D ) TOPOLOGY: Linear ( i i ) MOLECULE TYPE: Primer for HIV-II DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:17:

GTGGCAGACT TGTCTAAACG CACATCCCC      29

( 2 ) INFORMATION FOR SEQ ID NO:18:

( i ) SEQUENCE CHARACTERISTICS:
        ( A ) LENGTH: 26 nucleotides
        ( B ) TYPE: Nucleic acid
        ( C ) STRANDEDNESS: Single
        ( D ) TOPOLOGY: Linear ( i i ) MOLECULE TYPE: Probe for HIV-II DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:18:

GAGGAAAAGA AGTTCGGGGC AGAAGT      26

( 2 ) INFORMATION FOR SEQ ID NO:19:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: Probe for HIV-II DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:19:

CAACAAGAAA TGTTGCGACT GACCGTCT      28

( 2 ) INFORMATION FOR SEQ ID NO:20:

( i ) SEQUENCE CHARACTERISTICS:

( A ) LENGTH: 37 nucleotides
( B ) TYPE: Nucleic acid
( C ) STRANDEDNESS: Single
( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO:20:

CGTCGTCGTA TAATCCACCT ATCCCAGTAG GAGAAAT 37

( 2 ) INFORMATION FOR SEQ ID NO:21:

( i ) SEQUENCE CHARACTERISTICS:
( A ) LENGTH: 37 nucleotides
( B ) TYPE: Nucleic acid
( C ) STRANDEDNESS: Single
( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO:21:

CGTCGTCGTT TTGGTCCTTG TCTTATGTCC AGAATGC 37

( 2 ) INFORMATION FOR SEQ ID NO:22:

( i ) SEQUENCE CHARACTERISTICS:
( A ) LENGTH: 28 nucleotides
( B ) TYPE: Nucleic acid
( C ) STRANDEDNESS: Single
( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO:22:

ATAATCCACC TATCCCAGTA GGAGAAAT 28

( 2 ) INFORMATION FOR SEQ ID NO:23:

( i ) SEQUENCE CHARACTERISTICS:
( A ) LENGTH: 28 nucleotides
( B ) TYPE: Nucleic acid
( C ) STRANDEDNESS: Single
( D ) TOPOLOGY: Linear ( i i ) MOLECULE TYPE: Primer for HIV-I DNA ( i i i ) HYPOTHETICAL: No ( i v ) ANTI-SENSE: No ( v ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO:23:

TTTGGTCCTT GTCTTATGTC CAGAATGC 28

( 2 ) INFORMATION FOR SEQ ID NO:24:

( i ) SEQUENCE CHARACTERISTICS:
        ( A ) LENGTH: 40 nucleotides
        ( B ) TYPE: Nucleic acid
        ( C ) STRANDEDNESS: Single
        ( D ) TOPOLOGY: Linear ( i i ) MOLECULE TYPE: Primer for HIV-I DNA ( i i i ) HYPOTHETICAL: No ( i v ) ANTI-SENSE: No ( v ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO:24:

GATGGATGAC AAATAATCCA CCTATCCCAG TAGGAGAAAT 40

( 2 ) INFORMATION FOR SEQ ID NO:25:

( i ) SEQUENCE CHARACTERISTICS:
        ( A ) LENGTH: 40 nucleotides
        ( B ) TYPE: Nucleic acid
        ( C ) STRANDEDNESS: Single
        ( D ) TOPOLOGY: Linear ( i i ) MOLECULE TYPE: Primer for HIV-I DNA ( i i i ) HYPOTHETICAL: No ( i v ) ANTI-SENSE: No ( v ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO:25:

CTAAAGGGTT CCTTTGGTCC TTGTCTTATG TCCAGAATGC 40

( 2 ) INFORMATION FOR SEQ ID NO:26:

( i ) SEQUENCE CHARACTERISTICS:
        ( A ) LENGTH: 29 nucleotides
        ( B ) TYPE: Nucleic acid
        ( C ) STRANDEDNESS: Single
        ( D ) TOPOLOGY: Linear ( i i ) MOLECULE TYPE: Primer for hPV DNA ( i i i ) HYPOTHETICAL: No ( i v ) ANTI-SENSE: No (v i) ORIGINAL SOURCE: Synthetically prepared (v i i) IMMEDIATE SOURCE: Same (x) PUBLICATION INFORMATION: None (x i) SEQUENCE DESCRIPTION: SEQ ID NO:26:

GAGATGGGAA TCCATATGCT GTATGTGAT 29

(2) INFORMATION FOR SEQ ID NO:27:

(i) SEQUENCE CHARACTERISTICS:
(A) LENGTH: 29 nucleotides
(B) TYPE: Nucleic acid
(C) STRANDEDNESS: Single
(D) TOPOLOGY: Linear (i i) MOLECULE TYPE: Primer for hPV DNA (i i i) HYPOTHETICAL: No (i v) ANTI-SENSE: No (v i) ORIGINAL SOURCE: Synthetically prepared (v i i) IMMEDIATE SOURCE: Same (x) PUBLICATION INFORMATION: None (x i) SEQUENCE DESCRIPTION: SEQ ID NO:27:

GGACACAGTG GCTTTTGACA GTTAATACA 29

(2) INFORMATION FOR SEQ ID NO:28:

(i) SEQUENCE CHARACTERISTICS:
(A) LENGTH: 25 nucleotides
(B) TYPE: Nucleic acid
(C) STRANDEDNESS: Single
(D) TOPOLOGY: Linear (i i) MOLECULE TYPE: Primer for hPV DNA (i i i) HYPOTHETICAL: No (i v) ANTI-SENSE: No (v i) ORIGINAL SOURCE: Synthetically prepared (v i i) IMMEDIATE SOURCE: Same (x) PUBLICATION INFORMATION: None (x i) SEQUENCE DESCRIPTION: SEQ ID NO:28:

GATGGTCCAG CTGGACAAGC AGAAC 25

(2) INFORMATION FOR SEQ ID NO:29:

(i) SEQUENCE CHARACTERISTICS:
(A) LENGTH: 26 nucleotides
(B) TYPE: Nucleic acid
(C) STRANDEDNESS: Single
(D) TOPOLOGY: Linear (i i) MOLECULE TYPE: Primer for hPV DNA (i i i) HYPOTHETICAL: No (i v) ANTI-SENSE: No (v i) ORIGINAL SOURCE: Synthetically prepared (v i i) IMMEDIATE SOURCE: Same ( x ) PUBLICATION INFORMATION: None ( x i ) SEQUENCE DESCRIPTION: SEQ ID NO:29:

CCTAGTGTGC CCATTAACAG GTCTTC                         26

( 2 ) INFORMATION FOR SEQ ID NO:30:

( i ) SEQUENCE CHARACTERISTICS:
        ( A ) LENGTH: 29 nucleotides
        ( B ) TYPE: Nucleic acid
        ( C ) STRANDEDNESS: Single
        ( D ) TOPOLOGY: Linear ( i i ) MOLECULE TYPE: Primer for hPV DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:30:

GACACAGAAA ATGCTAGTGC TTATGCAGC                      29

( 2 ) INFORMATION FOR SEQ ID NO:31:

( i ) SEQUENCE CHARACTERISTICS:
        ( A ) LENGTH: 29 nucleotides
        ( B ) TYPE: Nucleic acid
        ( C ) STRANDEDNESS: Single
        ( D ) TOPOLOGY: Linear ( i i ) MOLECULE TYPE: Primer for hPV DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:31:

GGTGGACAAT CACCTGGATT TACTGCAAC                      29

( 2 ) INFORMATION FOR SEQ ID NO:32:

( i ) SEQUENCE CHARACTERISTICS:
        ( A ) LENGTH: 27 nucleotides
        ( B ) TYPE: Nucleic acid
        ( C ) STRANDEDNESS: Single
        ( D ) TOPOLOGY: Linear ( i i ) MOLECULE TYPE: Primer for hPV DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:32:

CCTGATCTGT GCACGGAACT GAACACT                        27

( 2 ) INFORMATION FOR SEQ ID NO:33:

( i ) SEQUENCE CHARACTERISTICS:
        ( A ) LENGTH: 32 nucleotides
        ( B ) TYPE: Nucleic acid
        ( C ) STRANDEDNESS: Single
        ( D ) TOPOLOGY: Linear ( i i ) MOLECULE TYPE: Primer for hPV DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:33:

CCCAGTGTTA GTTAGTTTTT CCAATGTGTC TG      32

( 2 ) INFORMATION FOR SEQ ID NO:34:

( i ) SEQUENCE CHARACTERISTICS:
        ( A ) LENGTH: 27 nucleotides
        ( B ) TYPE: Nucleic acid
        ( C ) STRANDEDNESS: Single
        ( D ) TOPOLOGY: Linear ( i i ) MOLECULE TYPE: Primer for hPV DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:34:

TGCCTGCGGT GCCAGAAACC GTTGAAT      27

( 2 ) INFORMATION FOR SEQ ID NO:35:

( i ) SEQUENCE CHARACTERISTICS:
        ( A ) LENGTH: 26 nucleotides
        ( B ) TYPE: Nucleic acid
        ( C ) STRANDEDNESS: Single
        ( D ) TOPOLOGY: Linear ( i i ) MOLECULE TYPE: Primer for hPV DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:35:

TGCTCGGTTG CAGCACGAAT GCCACT      26

( 2 ) INFORMATION FOR SEQ ID NO:36:

( i ) SEQUENCE CHARACTERISTICS:

(A) LENGTH: 28 nucleotides
            (B) TYPE: Nucleic acid
            (C) STRANDEDNESS: Single
            (D) TOPOLOGY: Linear (ii) MOLECULE TYPE: Primer for hPV DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:36:

GAGCCGAACC ACAACGTCAC ACAATGTT                                      28

(2) INFORMATION FOR SEQ ID NO:37:

(i) SEQUENCE CHARACTERISTICS:
            (A) LENGTH: 29 nucleotides
            (B) TYPE: Nucleic acid
            (C) STRANDEDNESS: Single
            (D) TOPOLOGY: Linear (ii) MOLECULE TYPE: Primer for hPV DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:37:

GGACACACAA AGGACAGGGT GTTCAGAAA                                     29

(2) INFORMATION FOR SEQ ID NO:38:

(i) SEQUENCE CHARACTERISTICS:
            (A) LENGTH: 27 nucleotides
            (B) TYPE: Nucleic acid
            (C) STRANDEDNESS: Single
            (D) TOPOLOGY: Linear (ii) MOLECULE TYPE: Primer for hCMV DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:38:

CATTCCCACT GACTTTCTGA CGCACGT                                       27

(2) INFORMATION FOR SEQ ID NO:39:

(i) SEQUENCE CHARACTERISTICS:
            (A) LENGTH: 24 nucleotides
            (B) TYPE: Nucleic acid
            (C) STRANDEDNESS: Single
            (D) TOPOLOGY: Linear ( i i ) MOLECULE TYPE: Primer for hPV DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:39:

GCGACTCAGA GGAAGAAAAC GATC  24

( 2 ) INFORMATION FOR SEQ ID NO:40:

( i ) SEQUENCE CHARACTERISTICS:
( A ) LENGTH: 25 nucleotides
( B ) TYPE: Nucleic acid
( C ) STRANDEDNESS: Single
( D ) TOPOLOGY: Linear ( i i ) MOLECULE TYPE: Primer for Mycobacterium
tuberculosis DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:40:

GAGATCGAGC TGGAGGATCC GTACG  25

( 2 ) INFORMATION FOR SEQ ID NO:41:

( i ) SEQUENCE CHARACTERISTICS:
( A ) LENGTH: 25 nucleotides
( B ) TYPE: Nucleic acid
( C ) STRANDEDNESS: Single
( D ) TOPOLOGY: Linear ( i i ) MOLECULE TYPE: Primer for Mycobacterium
tuberculosis DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:41:

AGCTGCAGCC CAAAGGTGTT GGACT  25

( 2 ) INFORMATION FOR SEQ ID NO:42:

( i ) SEQUENCE CHARACTERISTICS:
( A ) LENGTH: 21 nucleotides
( B ) TYPE: Nucleic acid
( C ) STRANDEDNESS: Single
( D ) TOPOLOGY: Linear ( i i ) MOLECULE TYPE: Primer for Mycobacterium
tuberculosis DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:42:

TCAGCCGCGT CCACGCCGCG A                    21

(2) INFORMATION FOR SEQ ID NO:43:

(i) SEQUENCE CHARACTERISTICS:
      (A) LENGTH: 20 nucleotides
      (B) TYPE: Nucleic acid
      (C) STRANDEDNESS: Single
      (D) TOPOLOGY: Linear (ii) MOLECULE TYPE: Primer for Mycobacterium tuberculosis DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:43:

CCTGCGAGCG TAGGCGTCGG                      20

(2) INFORMATION FOR SEQ ID NO:44:

(i) SEQUENCE CHARACTERISTICS:
      (A) LENGTH: 20 nucleotides
      (B) TYPE: Nucleic acid
      (C) STRANDEDNESS: Single
      (D) TOPOLOGY: Linear (ii) MOLECULE TYPE: Primer for Mycobacterium avium DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:44:

GAGATCGCCA CCTTCGGCAA                      20

(2) INFORMATION FOR SEQ ID NO:45:

(i) SEQUENCE CHARACTERISTICS:
      (A) LENGTH: 20 nucleotides
      (B) TYPE: Nucleic acid
      (C) STRANDEDNESS: Single
      (D) TOPOLOGY: Linear (ii) MOLECULE TYPE: Primer for Mycobacterium avium DNA (iii) HYPOTHETICAL: No (iv) ANTI-SENSE: No (v) ORIGINAL SOURCE: Synthetically prepared (vii) IMMEDIATE SOURCE: Same (x) PUBLICATION INFORMATION: None (xi) SEQUENCE DESCRIPTION: SEQ ID NO:45:

GAGCAGTTCG GTGGCGTTCA 20

(2) INFORMATION FOR SEQ ID NO:46:

(i) SEQUENCE CHARACTERISTICS:
        (A) LENGTH: 25 nucleotides
        (B) TYPE: Nucleic acid
        (C) STRANDEDNESS: Single
        (D) TOPOLOGY: Linear (ii) MOLECULE TYPE: Primer for hCMV DNA (iii) HYPOTHETICAL: No (iv) ANTI-SENSE: No (v) ORIGINAL SOURCE: Synthetically prepared (vii) IMMEDIATE SOURCE: Same (x) PUBLICATION INFORMATION: U.S. 5,147,777

(xi) SEQUENCE DESCRIPTION: SEQ ID NO:46:

GAGGCTATTG TAGCCTACAC TTTGG 25

(2) INFORMATION FOR SEQ ID NO:47:

(i) SEQUENCE CHARACTERISTICS:
        (A) LENGTH: 25 nucleotides
        (B) TYPE: Nucleic acid
        (C) STRANDEDNESS: Single
        (D) TOPOLOGY: Linear (ii) MOLECULE TYPE: Primer for hCMV DNA (iii) HYPOTHETICAL: No (iv) ANTI-SENSE: No (v) ORIGINAL SOURCE: Synthetically prepared (vii) IMMEDIATE SOURCE: Same (x) PUBLICATION INFORMATION: U.S. 5,147,777

(xi) SEQUENCE DESCRIPTION: SEQ ID NO:47:

CAGCACCATC CTCCTCTTCC TCTGG 25

(2) INFORMATION FOR SEQ ID NO:48:

(i) SEQUENCE CHARACTERISTICS:
        (A) LENGTH: 24 nucleotides
        (B) TYPE: Nucleic acid
        (C) STRANDEDNESS: Single
        (D) TOPOLOGY: Linear (ii) MOLECULE TYPE: Primer for hCMV DNA (iii) HYPOTHETICAL: No (iv) ANTI-SENSE: No (v) ORIGINAL SOURCE: Synthetically prepared (vii) IMMEDIATE SOURCE: Same (x) PUBLICATION INFORMATION: None (xi) SEQUENCE DESCRIPTION: SEQ ID NO:48:

TGAGGTCGTG GAACTTGATG GCGT                                                                                              24

(2) INFORMATION FOR SEQ ID NO:49:

(i) SEQUENCE CHARACTERISTICS:
        (A) LENGTH: 30 nucleotides
        (B) TYPE: Nucleic acid
        (C) STRANDEDNESS: Single
        (D) TOPOLOGY: Linear (ii) MOLECULE TYPE: Probe for hCMV DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: U.S. 5,147,777

(xi) SEQUENCE DESCRIPTION: SEQ ID NO:49:

GACACAGTGT CCTCCCGCTC CTCCTGAGCA                                                                                        30

(2) INFORMATION FOR SEQ ID NO:50:

(i) SEQUENCE CHARACTERISTICS:
        (A) LENGTH: 30 nucleotides
        (B) TYPE: Nucleic acid
        (C) STRANDEDNESS: Single
        (D) TOPOLOGY: Linear (ii) MOLECULE TYPE: Probe for hCMV DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: U.S. 5,147,777

(xi) SEQUENCE DESCRIPTION: SEQ ID NO:50:

GTGGAAGGCG GCTCGCTGGA AGCCGGTCGT                                                                                        30

(2) INFORMATION FOR SEQ ID NO:51:

(i) SEQUENCE CHARACTERISTICS:
        (A) LENGTH: 33 nucleotides
        (B) TYPE: Nucleic acid
        (C) STRANDEDNESS: Single
        (D) TOPOLOGY: Linear (ii) MOLECULE TYPE: Probe for hPV DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:51:

| GGAACAACAT TAGAACAGCA ATACAACAAA CCG | 33 |

(2) INFORMATION FOR SEQ ID NO:52:

(i) SEQUENCE CHARACTERISTICS:
        (A) LENGTH: 32 nucleotides
        (B) TYPE: Nucleic acid
        (C) STRANDEDNESS: Single
        (D) TOPOLOGY: Linear (ii) MOLECULE TYPE: Probe for hPV DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:52:

| AATATTGTAA CCTTTTGTTG CAAGTGTGAC TC | 32 |

(2) INFORMATION FOR SEQ ID NO:53:

(i) SEQUENCE CHARACTERISTICS:
        (A) LENGTH: 30 nucleotides
        (B) TYPE: Nucleic acid
        (C) STRANDEDNESS: Single
        (D) TOPOLOGY: Linear (ii) MOLECULE TYPE: Probe for hPV DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:53:

| CCTATAGGTG GTTTGCAACC AATTAAACAC | 30 |

(2) INFORMATION FOR SEQ ID NO:54:

(i) SEQUENCE CHARACTERISTICS:
        (A) LENGTH: 35 nucleotides
        (B) TYPE: Nucleic acid
        (C) STRANDEDNESS: Single
        (D) TOPOLOGY: Linear (ii) MOLECULE TYPE: Probe for hPV DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:54:

| GAGGTATTTG AATTTGCATT TAAAGATTTA TTTGT | 35 |

(2) INFORMATION FOR SEQ ID NO:55:

( i ) SEQUENCE CHARACTERISTICS:
   ( A ) LENGTH: 27 nucleotides
   ( B ) TYPE: Nucleic acid
   ( C ) STRANDEDNESS: Single
   ( D ) TOPOLOGY: Linear ( i i ) MOLECULE TYPE: Probe for hPV DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:55:

GCAAGACAGT ATTGGAACTT ACAGAGG 27

( 2 ) INFORMATION FOR SEQ ID NO:56:

( i ) SEQUENCE CHARACTERISTICS:
   ( A ) LENGTH: 27 nucleotides
   ( B ) TYPE: Nucleic acid
   ( C ) STRANDEDNESS: Single
   ( D ) TOPOLOGY: Linear ( i i ) MOLECULE TYPE: Probe for hPV DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:56:

GTGTTGTAAG TGTGAAGCCA GATTTGA 27

( 2 ) INFORMATION FOR SEQ ID NO:57:

( i ) SEQUENCE CHARACTERISTICS:
   ( A ) LENGTH: 30 nucleotides
   ( B ) TYPE: Nucleic acid
   ( C ) STRANDEDNESS: Single
   ( D ) TOPOLOGY: Linear ( i i ) MOLECULE TYPE: Probe for Mycobacterium
            tuberculosis DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:57:

GAGCAGATTG CGGCCACCGC AGCGATTTCG 30

( 2 ) INFORMATION FOR SEQ ID NO:58:

( i ) SEQUENCE CHARACTERISTICS:
   ( A ) LENGTH: 20 nucleotides
   ( B ) TYPE: Nucleic acid
   ( C ) STRANDEDNESS: Single (D) TOPOLOGY: Linear (ii) MOLECULE TYPE: Probe for Mycobacterium
tuberculosis DNA (iii) HYPOTHETICAL: No (iv) ANTI-SENSE: No (v) ORIGINAL SOURCE: Synthetically prepared (vii) IMMEDIATE SOURCE: Same (x) PUBLICATION INFORMATION: None (xi) SEQUENCE DESCRIPTION: SEQ ID NO:58:

CTCGTCCAGC GCCGCTTCGG                         20

(2) INFORMATION FOR SEQ ID NO:59:

(i) SEQUENCE CHARACTERISTICS:
(A) LENGTH: 20 nucleotides
(B) TYPE: Nucleic acid
(C) STRANDEDNESS: Single
(D) TOPOLOGY: Linear (ii) MOLECULE TYPE: Probe for Mycobacterium
avium DNA (iii) HYPOTHETICAL: No (iv) ANTI-SENSE: No (v) ORIGINAL SOURCE: Synthetically prepared (vii) IMMEDIATE SOURCE: Same (x) PUBLICATION INFORMATION: None (xi) SEQUENCE DESCRIPTION: SEQ ID NO:59:

TGGATCTCGT TGTTCGGGTC                         20

(2) INFORMATION FOR SEQ ID NO:60:

(i) SEQUENCE CHARACTERISTICS:
(A) LENGTH: 30 nucleotides
(B) TYPE: Nucleic acid
(C) STRANDEDNESS: Single
(D) TOPOLOGY: Linear (ii) MOLECULE TYPE: Probe for Mycobacterium
avium DNA (iii) HYPOTHETICAL: No (iv) ANTI-SENSE: No (v) ORIGINAL SOURCE: Synthetically prepared (vii) IMMEDIATE SOURCE: Same (x) PUBLICATION INFORMATION: Unknown (xi) SEQUENCE DESCRIPTION: SEQ ID NO:60:

GACCAGATCG CTGCCACCGC GGCCATCTCC              30

(2) INFORMATION FOR SEQ ID NO:61:

(i) SEQUENCE CHARACTERISTICS:
(A) LENGTH: 30 nucleotides
(B) TYPE: Nucleic acid
(C) STRANDEDNESS: Single
(D) TOPOLOGY: Linear (i i) MOLECULE TYPE: Probe for Mycobacterium fortuitum DNA (i i i) HYPOTHETICAL: No (i v) ANTI-SENSE: No (v i) ORIGINAL SOURCE: Synthetically prepared (v i i) IMMEDIATE SOURCE: Same (x) PUBLICATION INFORMATION: Unknown (x i) SEQUENCE DESCRIPTION: SEQ ID NO:61:

GAGCAGATCG CTGCCACCGC CGGTATCTCC 30

(2) INFORMATION FOR SEQ ID NO:62:

(i) SEQUENCE CHARACTERISTICS:
(A) LENGTH: 30 nucleotides
(B) TYPE: Nucleic acid
(C) STRANDEDNESS: Single
(D) TOPOLOGY: Linear (i i) MOLECULE TYPE: Probe for hCMV DNA (i i i) HYPOTHETICAL: No (i v) ANTI-SENSE: No (v i) ORIGINAL SOURCE: Synthetically prepared (v i i) IMMEDIATE SOURCE: Same (x) PUBLICATION INFORMATION: Unknown (x i) SEQUENCE DESCRIPTION: SEQ ID NO:62:

GGTCATCGCC GTAGTAGATG CGTAAGGCCT 30

(2) INFORMATION FOR SEQ ID NO:63:

(i) SEQUENCE CHARACTERISTICS:
(A) LENGTH: 25 nucleotides
(B) TYPE: Nucleic acid
(C) STRANDEDNESS: Single
(D) TOPOLOGY: Linear (i i) MOLECULE TYPE: Primer for HSV-1 DNA (i i i) HYPOTHETICAL: No (i v) ANTI-SENSE: No (v i) ORIGINAL SOURCE: Synthetically prepared (v i i) IMMEDIATE SOURCE: Same (x) PUBLICATION INFORMATION: Unknown (x i) SEQUENCE DESCRIPTION: SEQ ID NO:63:

CCGGGAGATG GGGGAGGCTA ACTGA 25

(2) INFORMATION FOR SEQ ID NO:64:

(i) SEQUENCE CHARACTERISTICS:
(A) LENGTH: 25 nucleotides
(B) TYPE: Nucleic acid
(C) STRANDEDNESS: Single
(D) TOPOLOGY: Linear (i i) MOLECULE TYPE: Primer for HSV-1 DNA (i i i) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO:64:

GGGGTGGGGA AAAGGAAGAA ACGCG                                                                         2 5

( 2 ) INFORMATION FOR SEQ ID NO:65:

( i ) SEQUENCE CHARACTERISTICS:
        ( A ) LENGTH: 33 nucleotides
        ( B ) TYPE: Nucleic acid
        ( C ) STRANDEDNESS: Single
        ( D ) TOPOLOGY: Linear ( i i ) MOLECULE TYPE: Probe for HSV-1 DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO:65:

AAAGACAGAA TAAAACGCAC GGGTGTTGGG TCG                                                                 3 3